(12) United States Patent
Cheng et al.

(10) Patent No.: US 10,318,705 B2
(45) Date of Patent: Jun. 11, 2019

(54) METHODS FOR THE ANALYSIS OF HIGH RESOLUTION MELT CURVE DATA

(71) Applicant: LIFE TECHNOLOGIES CORPORATION, Carlsbad, CA (US)

(72) Inventors: Francis T. Cheng, Palo Alto, CA (US); Chengyong Yang, Foster City, CA (US); Casey McFarland, San Francisco, CA (US); Ying Wang, Chicago, IL (US)

(73) Assignee: Life Technologies Corporation, Carlsbad, CA (US)

( * ) Notice: Subject to any disclaimer, the term of this patent is extended or adjusted under 35 U.S.C. 154(b) by 343 days.

(21) Appl. No.: 15/159,717

(22) Filed: May 19, 2016

(65) Prior Publication Data
US 2016/0342734 A1 Nov. 24, 2016

Related U.S. Application Data

(63) Continuation of application No. 13/850,287, filed on Mar. 25, 2013, now abandoned, which is a
(Continued)

(51) Int. Cl.
| | |
|---|---|
| G01N 21/64 | (2006.01) |
| G01N 25/04 | (2006.01) |
| C12Q 1/6816 | (2018.01) |
| C12Q 1/6827 | (2018.01) |

(Continued)

(52) U.S. Cl.
CPC .......... *G06F 19/22* (2013.01); *C12Q 1/6816* (2013.01); *C12Q 1/6827* (2013.01);
(Continued)

(58) Field of Classification Search
None
See application file for complete search history.

(56) References Cited

U.S. PATENT DOCUMENTS

| | | |
|---|---|---|
| 2011/0105345 A1 | 5/2011 | Cheng et al. |
| 2013/0218476 A1 | 8/2013 | Cheng et al. |

FOREIGN PATENT DOCUMENTS

| | | |
|---|---|---|
| WO | 2007/035806 A2 | 3/2007 |

OTHER PUBLICATIONS

Daniels, K. & Giraud-Carrier, C. Learning the Threshold in Hierarchical Agglomerative Clustering. in International Conference on Machine Learning and Applications 270-278 (IEEE, 2006).*

(Continued)

*Primary Examiner* — Soren Harward
(74) *Attorney, Agent, or Firm* — Lana Akopyan; Michael Mauriel; Mauriel Kapouytian Woods LLP

(57) ABSTRACT

The present application provides for various embodiments of methods for the analysis of high resolution melt (HRM) curve data; where statistical assay variations in melt curve data may result from system noise in an analysis system. Such system noise may arise from various sources, such as the thermal non-uniformity of a thermocycler block in a thermal cycler apparatus, a detection system, etc. Additionally, various methods for the analysis of HRM curve data may provide an identification of a sample without the need for a user inputted information.

20 Claims, 16 Drawing Sheets

Related U.S. Application Data continuation of application No. 12/848,967, filed on Aug. 2, 2010, now abandoned.

(60) Provisional application No. 61/230,646, filed on Jul. 31, 2009.

(51) Int. Cl.
 G06F 19/22 (2011.01)
 G06F 19/24 (2011.01)

(52) U.S. Cl.
 CPC .......... G01N 21/6428 (2013.01); G01N 25/04 (2013.01); G06F 19/24 (2013.01); G01N 2021/6439 (2013.01)

(56) References Cited

OTHER PUBLICATIONS

Davidson, I. & Ravi, S. S. Agglomerative hierarchical clustering with constraints: Theoretical and empirical results. in Knowledge Discovery in Databases 3721, 59-70 (2005).*

Dotan-Cohen, D., Melkman, A. A. & Kasif, S. Hierarchical tree snipping: Clustering guided by prior knowledge. Bioinformatics 23, 3335-3342 (2007).*

Duda et al., "Hierarchical Clustering," Pattern Classification, 2001, 2nd Edition, pp. 550-557.

Reed et al., "High-resolution DNA melting analysis for simple and efficient molecular diagnostics," Pharmacogenomics, 2007, vol. 8, No. 6, pp. 597-608.

Seipp et al., "Unlabeled Oligonucleotides as Internal Temperature Controls for Genotyping by Amplicon Melting," Journal of Molecular Diagnostics, vol. 9, No. 3, pp. 284-289.

Vandersteen et al., "Identifying common genetic variants by high-resolution melting," Clinical Chemistry, 2007, vol. 53, No. 7, pp. 1191-1198.

Wittwer et al., "High-Resolution Genotyping by Amplicon Melting Analysis Using LCGreen," Clinical Chemistry, 2003, vol. 49, No. 6, pp. 853-860.

Xu et al., "Survey of Clustering Algorithms," IEEE Transactions on Neural Networks, 2005, vol. 16, No. 3, pp. 645-678.

Zhou et al., "High-resolution DNA melting analysis for simultaneous mutation scanning and genotyping in solution," Clinical Chemistry, 2005, vol. 51, No. 10, pp. 1770-1777.

* cited by examiner

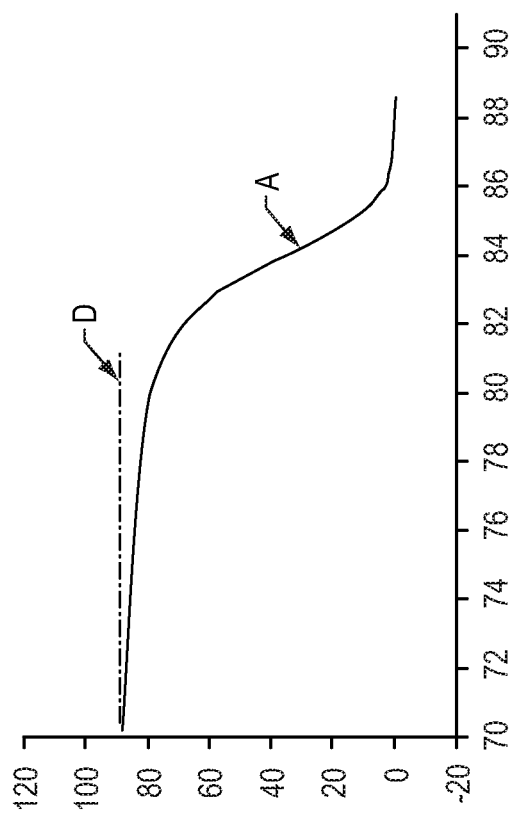
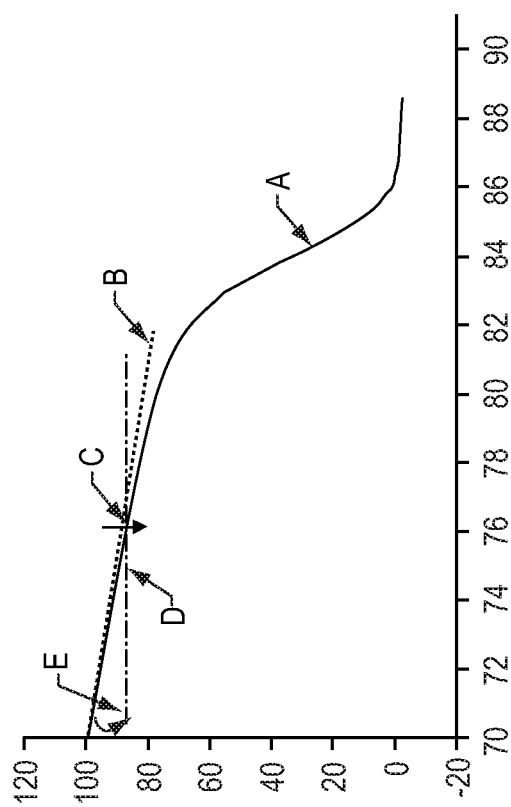
FIG. 7A
FIG. 7B

FIG. 13

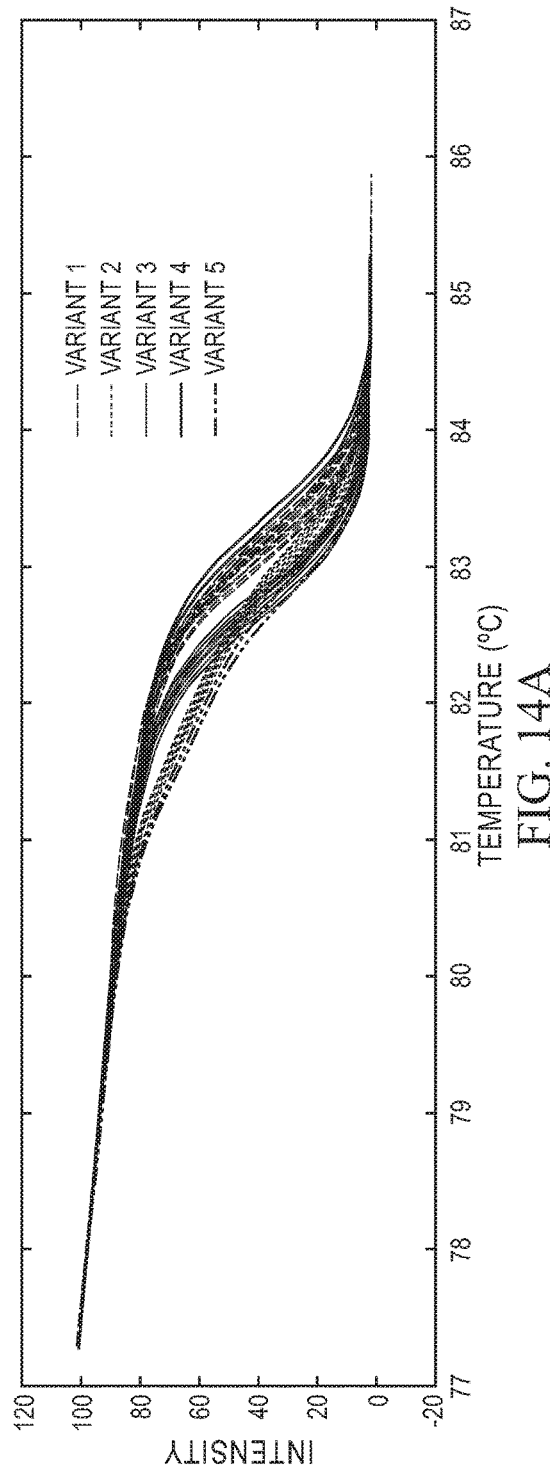
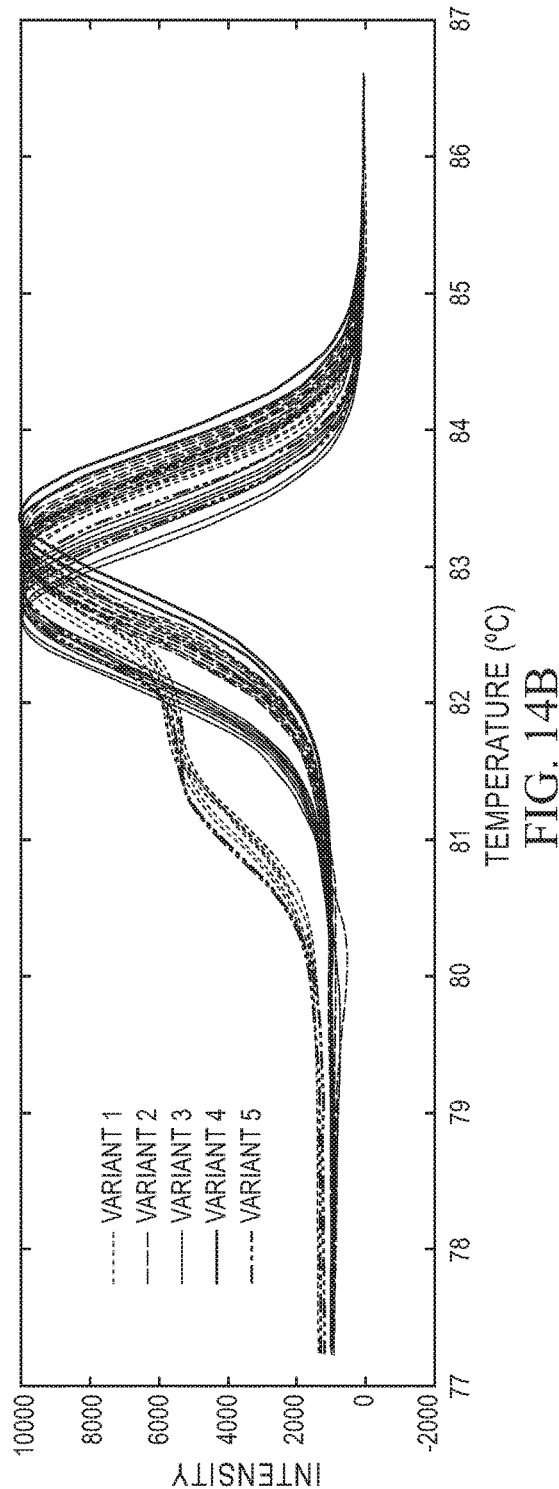
FIG. 14A
FIG. 14B

| Well Index | No Control | With Control |
|---|---|---|
| 39 | variant1 | variant1 |
| 40 | variant4 | WT-CONTROL |
| 41 | variant2 | WT |
| 42 | variant1 | variant1 |
| 43 | variant2 | WT |
| 44 | variant2 | WT |
| 45 | variant2 | WT |
| 46 | variant1 | variant1 |
| 47 | variant2 | WT |
| 48 | variant3 | variant2 |
| 49 | variant3 | variant2 |
| 50 | variant3 | variant2 |
| 51 | variant1 | variant1 |
| 52 | variant2 | WT |
| 53 | variant2 | WT |
| 54 | variant1 | variant1 |
| 55 | variant2 | WT |
| 56 | variant2 | WT |
| 57 | variant2 | WT |
| 58 | variant1 | variant1 |
| 59 | variant2 | WT |
| 60 | variant3 | variant2 |
| 61 | variant3 | variant2 |
| 62 | variant3 | variant2 |
| 63 | variant1 | variant1 |
| 64 | variant2 | WT |
| 65 | variant2 | WT |
| 66 | variant1 | variant1 |
| 67 | variant2 | WT |
| 68 | variant2 | WT |
| 69 | variant2 | WT |
| 70 | variant1 | variant1 |
| 71 | variant2 | WT |
| 72 | variant3 | variant2 |
| 73 | variant3 | variant2 |
| 74 | variant3 | variant2 |
| 75 | variant1 | variant1 |
| 76 | variant4 | WT |

FIG. 16

METHODS FOR THE ANALYSIS OF HIGH RESOLUTION MELT CURVE DATA

CROSS REFERENCE TO RELATED APPLICATION

This application is a continuation of U.S. application Ser. No. 13/850,287 filed Mar. 25, 2013, which is a continuation of U.S. application Ser. No. 12/848,967 filed Aug. 2, 2010, now Abandoned, which claims a priority benefit under 35 U.S.C. § 119(e) from U.S. Patent Application No. 61/230,646 filed Jul. 31, 2009, all of which are incorporated herein by reference.

FIELD

The field of disclosure of relates to methods for analyzing high resolution melt curve data, especially as the analysis relates to data for which the melting temperatures of the plurality of samples varies by only a fraction of a degree.

BACKGROUND

DNA amplification methods provide a powerful and widely used tool for genomic analysis. Polymerase chain reaction (PCR) methods, for example, permit quantitative analysis to determine DNA copy number, sample source quantitation, and transcription analysis of gene expression. High resolution melt (HRM) analysis is an important tool used for characterization of amplification products, by way of example, for genotyping, mutation screening, methylation analysis or to ensure that the intended product was amplified. Various HRM curve methods may allow for the detection of single base changes in specific regions of the genome, such as single nucleotide polymorphisms (SNPs). SNP analysis and other techniques facilitate the identification of mutations associated with specific diseases and conditions, for example, but not limited by, various cancers, thalassemia, neonatal diabetes, and rheumatoid arthritis. Melt curve analysis can indicate if multiple products are amplified, non-specific amplification has occurred or if there were assay amplification issues such as primer-dimmer formation. High resolution melt analysis can also be useful for the analysis of other biological samples including but not limited by proteins to analyze the signal changes within a sample, or between samples with changing temperature.

Statistical assay variations in melt curve data may result from system noise in an analysis system, such as the thermal non-uniformity of a thermocycler block in a thermal cycler apparatus. For certain applications, the melting point shift between samples may be only fractions of a degree. In the case of SNP analysis, the SNP mutations may shift the melting point temperature by no more than 0.2° C. Providing methods for analysis of such data is tantamount to providing the analyses mentioned in the above. Additionally, providing a method for which a control sample is not required in order to make an identification of a sample may provide enhanced quality of the identification made. Such methods yielding a sample identification in which a control is not required may be more robust by, for example, but not limited by, avoiding the misidentification of a control sample, or by interference caused by contaminants in a control sample.

Accordingly, there is a need in the art for methods of analyzing small differences in melting curves in the presence of the inherent noise of the analysis, which methods may additionally provide enhanced quality of identification by utilizing unbiased processes not requiring a control.

BRIEF DESCRIPTION OF THE DRAWINGS

FIG. 7A and FIG. 7B illustrate estimating an asymptote according to various embodiments of methods for the analysis of HRM curve data for the low temperature region of graphs, such as those shown in FIG. 6.

FIG. 13 is a table depicting how various methods for the analysis of HRM curve data may be utilized in the example of the analysis of EMCD for genotyping.

FIGS. 14A and 14B depict an exemplary set of EMCD for genotyping on which various embodiments of a method for the analysis of HRM curve data may be performed.

FIG. 16 is a table depicting the results of using an association of an HRM curve genotyping control with selected HRM samples according to various embodiments of a method for the analysis of HRM data depicted in FIGS. 15A and 15B.

DETAILED DESCRIPTION

Figure 1:
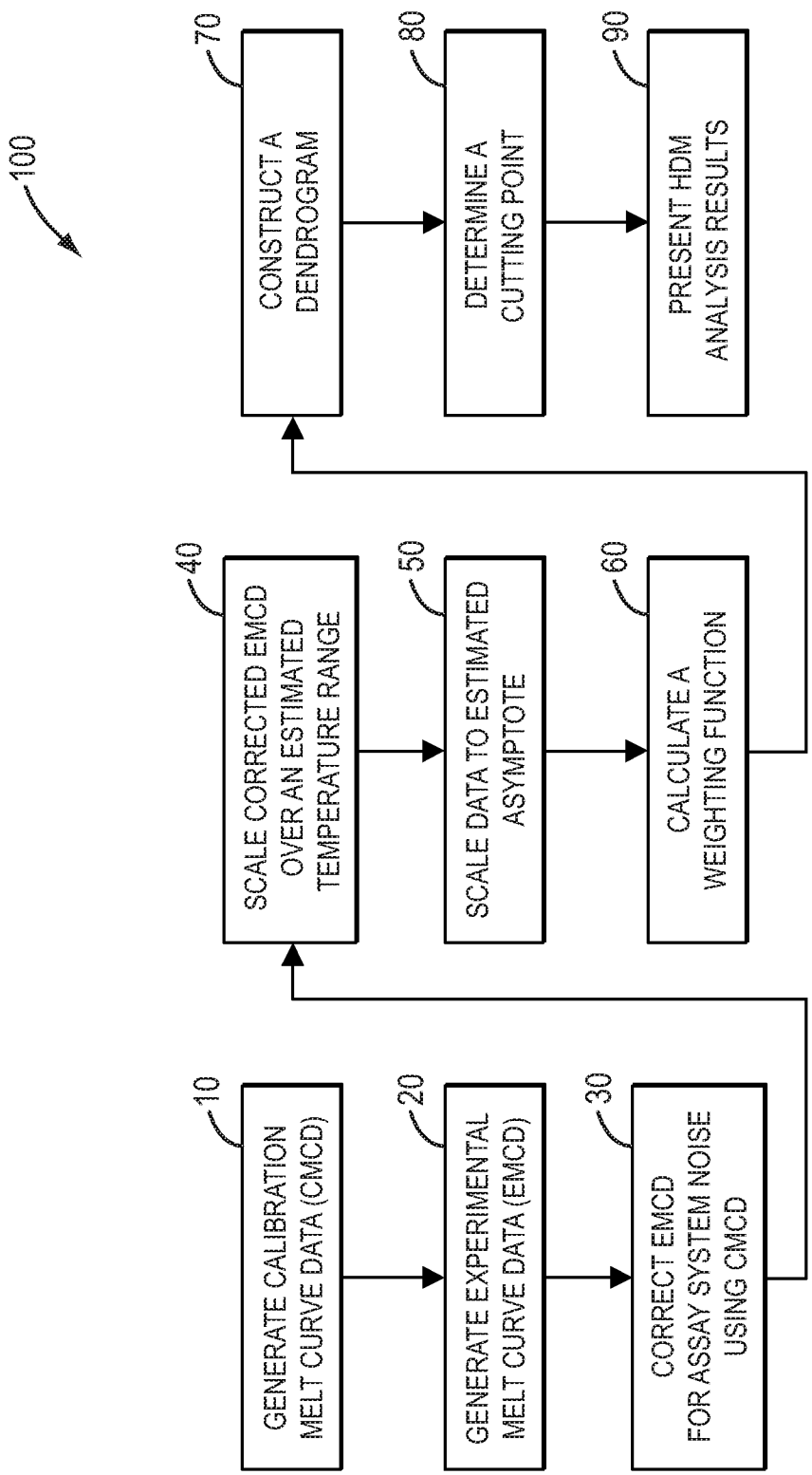
FIG. 1 is a flow chart that depicts various embodiments of methods for the analysis of HRM curve data.

What is disclosed herein are various embodiments of methods for analyzing high resolution melt curve (HRM) data, where the differences in the melting points between various samples are small. For example, various embodiments of methods for analyzing HRM curve data address samples sets where the differences in melting points may vary by only fractions of degrees. According to various embodiments of methods for analyzing HRM curve data, a calibration set of melt curve data may be used as a basis for correcting experimental sets of melt curve data, for example, with respect to assay system variance or noise. According to various embodiments, the HRM curve data may be processed using curve-fitting techniques. In various embodiments of methods for analyzing HRM curve data, various embodiments of a cluster analysis method utilizing a weighting function may be used to in the analysis of samples. Various embodiments of methods for analyzing HRM curve data which using embodiments of a cluster analysis method utilizing a weighting function may be used without having to run a control sample. Such methods yielding a sample identification in which a control is not required may be more robust by, for example, but not limited by, avoiding the misidentification of a control sample, or by interference caused by contaminants in a control sample.

One known approach for DNA melting curve analysis utilizes fluorescence monitoring with intercalating double-strand-DNA specific dyes, such as for example, SYBR Green. The SYBR Green dye attaches to the DNA as double-stranded DNA amplification products are formed, and continues to bind to the DNA as long as the DNA remains double-stranded. When melting temperatures are reached, the denaturation or melting of the double-stranded DNA is indicated and can be observed by a significant reduction in fluorescence, as SYBR Green dissociates from the melted strand. The detected dye fluorescence intensity typically decreases about 1000-fold during the melting process. Plotting fluorescence as a function of temperature as the sample heats through the dissociation temperature produces a DNA melting curve. The shape and position of the DNA melting curve is a function of the DNA sequence, length, and GC/AT content.

Further, various approaches for validating the integrity of PCR reactions rely on melting curve analysis to ensure the intended product was amplified. Melt curve analysis can identify untoward assay amplification issues versus the formation of a single, targeted product. For example, but not limited by, melting curve analysis may discriminate between a single, targeted product and non-specific amplification, primer-dimmer formation, as well as multiple amplified products. Melting curve analysis can also be used to differentiate the various products of multiplexed DNA amplification, and to extend the dynamic range of quantitative PCR. DNA melting curve analysis is also used as a powerful tool for optimizing PCR thermal cycling conditions, because the point at which DNA fragments or other material melts and separate can be more accurately pinpointed.

In some embodiments, HRM curve analysis methods calculate and display the first derivative of multi-component dye intensity data versus temperature, i.e., the differential melting curve. The melting temperature, $T_m$, at a peak of the differential melting curve can be used to characterize the product of a biochemical reaction. A sample with multiple amplification products will show multiple peaks in the differential melt curve. In some embodiments, melting curve detection involves very precise measurements of temperature and allows for the identification of a sample using the melting temperature, $T_m$. The determination of $T_m$ using various embodiments of methods for differential dissociation and melting curve detection is disclosed in related in U.S. patent application Ser. No. 12/020,369, which is incorporated herein by reference in its entirety.

Figure 3:
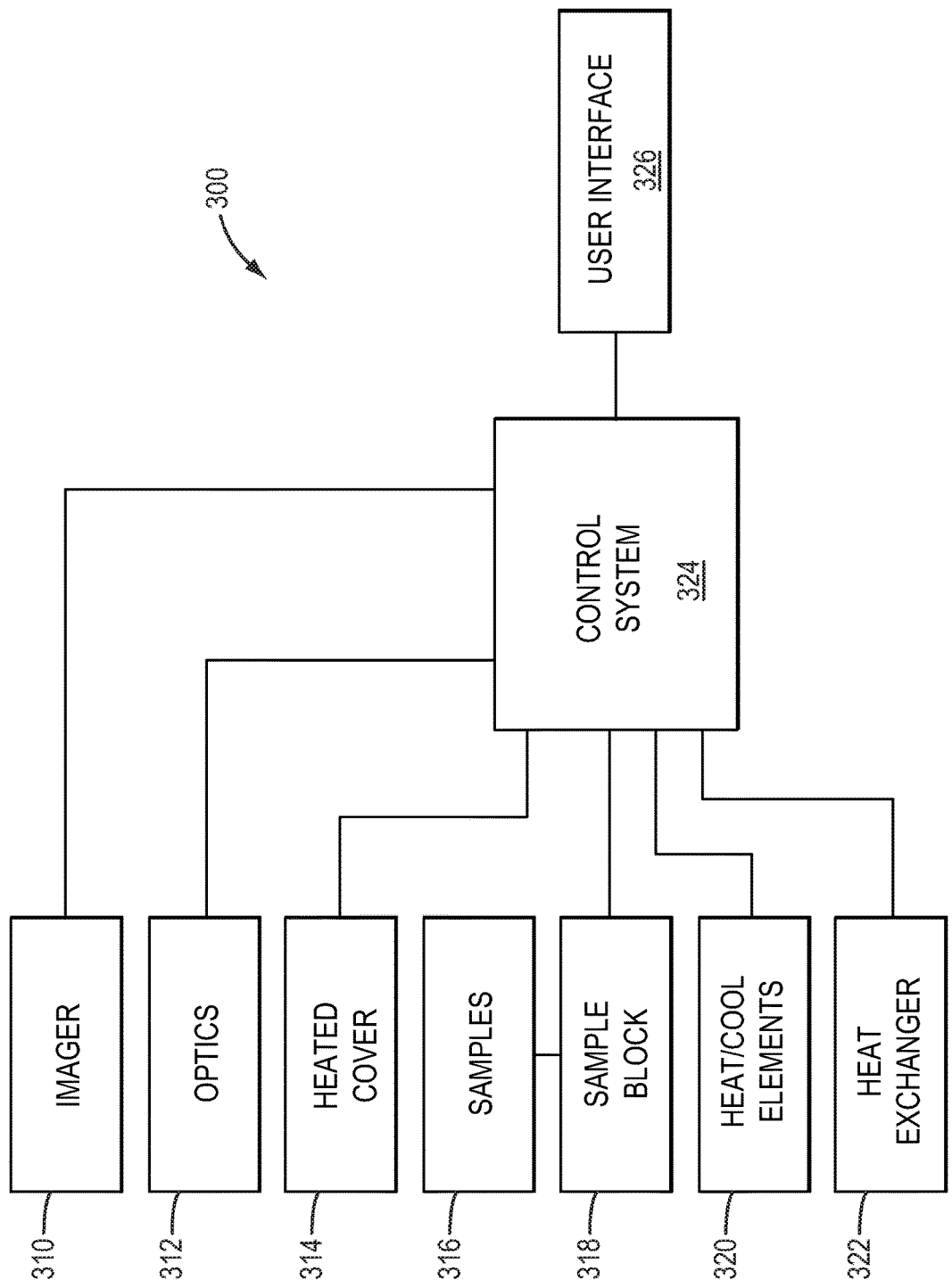
FIG. 3 depicts various embodiments of an apparatus useful in the generation of HRM curve data.

According to various embodiments of a thermal cycler instrument 300, as shown in FIG. 3, a thermal cycling instrument may include a heated cover 314 that is placed over a plurality of samples 316 contained in a sample support device. In various embodiments, a sample support device may be a glass or plastic substrate material having a plurality of sample regions, which sample regions may have a cover between the sample regions and heated cover 314. Some examples of a sample support device may include, but are not limited by, sample tubes or vials, a multi-well plate, such as a standard microtiter plate (i.e. for example, but not limited by, a 96-well, a 384-well plate, 1536-well plate, etc), a microcard, or a substantially planar support, such as a glass or plastic slide. The sample regions in various embodiments of a sample support device may include depressions, indentations, ridges, and combinations thereof, patterned in regular or irregular arrays formed on the surface of the substrate. Various embodiments of a thermal cycler instrument 300 may include a thermal block assembly, which may include a sample block 318, as well as elements for heating and cooling 320, and a heat exchanger 322.

Figure 4:
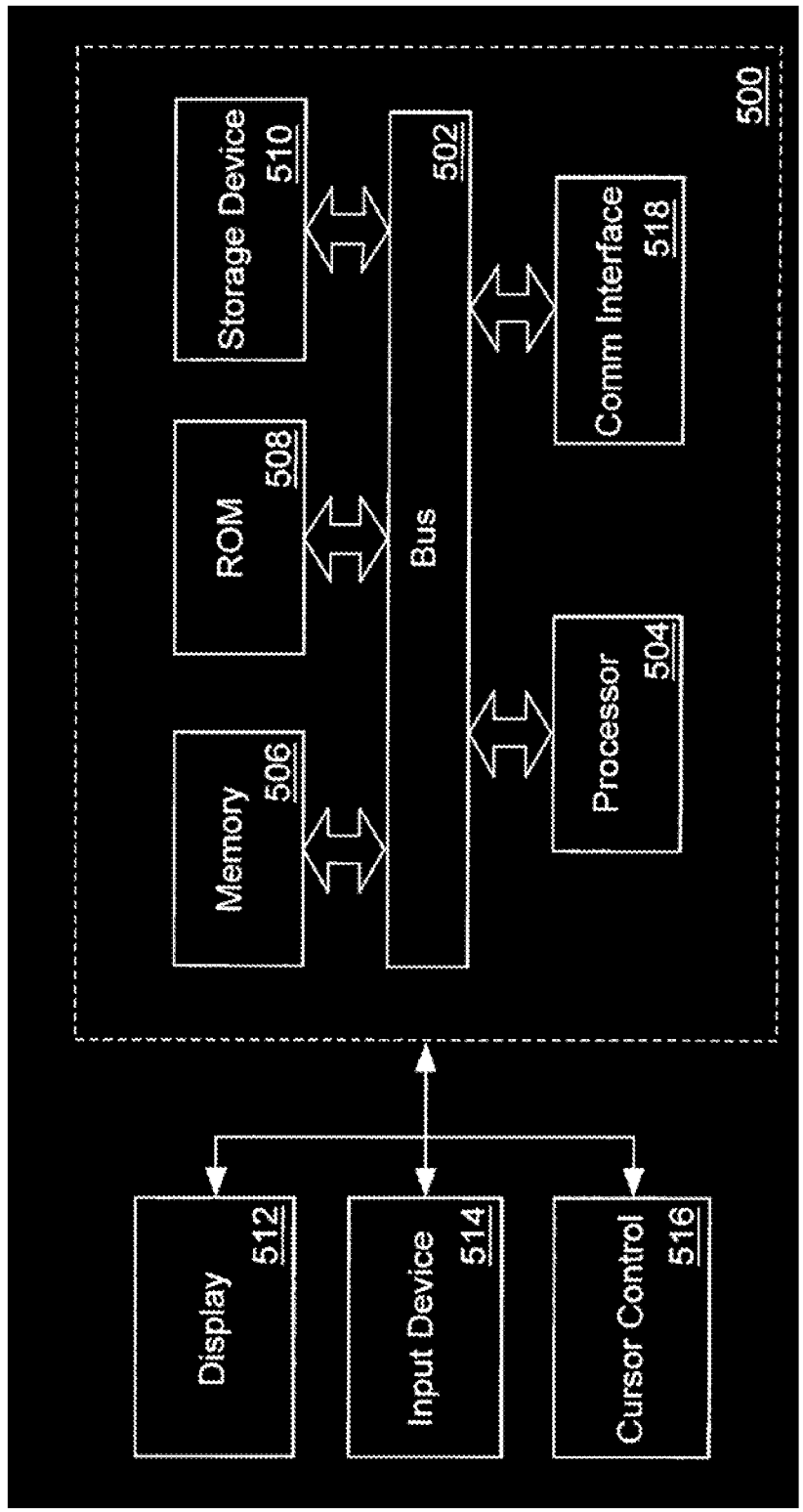
FIG. 4 is a block diagram that illustrates a computer system according to various embodiments upon which embodiments of methods for the analysis of HRM melt curves may be implemented.

Additionally, various embodiments of a thermal cycling system 300 may have a detection system. A detection system may have an illumination source that emits electromagnetic energy (not shown), a detector or imager 310, for receiving electromagnetic energy from samples 316 in sample support device, and optics 312, which may be located between the illumination source and detector or imager 310. For various embodiments of a thermal cycler instrument 300, a control system 324 may be used to control, for example, but not limited by, the functions of the detection, heated cover, and thermal block assembly. The control system 324 may be accessible to an end user through user interface 326 of a thermal cycler instrument 300. In addition to a user interface system 326, a computer system 500, as depicted in FIG. 4 may serve as to provide control of various functions of a thermal cycler instrument. Additionally, computer system 500 may provide data processing, display and report preparation functions. All such instrument control functions may be dedicated locally to the thermal cycler instrument, or computer system 500 may provide remote control of part or all of the control, analysis, and reporting functions, as will be discussed in more detail subsequently.

FIG. 4 is a block diagram that illustrates a computer system 500, according to various embodiments, upon which embodiments of methods for the analysis of HRM melt curves may be implemented. Computer system 500 includes a bus 502 or other communication mechanism for communicating information, and a processor 504 coupled with bus 502 for processing information. Computer system 500 also includes a memory 506, which can be a random access memory (RAM) or other dynamic storage device, coupled to bus 502, and instructions to be executed by processor 504. Memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

Computer system 500 may be coupled via bus 502 to a display 512, such as a cathode ray tube (CRT) or liquid crystal display (LCD), for displaying information to a computer user. An input device 514, including alphanumeric and other keys, is coupled to bus 502 for communicating information and command selections to processor 504. Another type of user input device is cursor control 516, such as a mouse, a trackball or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. A computer system 500 may provide the determination of a result for a set of sample data, and a level of confidence for a result. Consistent with certain implementations of the invention, such results and confidence values are provided by computer system 500 in response to processor 504 executing one or more sequences of one or more instructions contained in memory 506. Such instructions may be read into memory 506 from another computer-readable medium, such as storage device 510. Execution of the sequences of instructions contained in memory 506 causes processor 504 to perform the process states described herein. Alternatively hard-wired circuitry may be used in place of or in combination with software instructions to implement the invention. Thus implementations of the invention are not limited to any specific combination of hardware circuitry and software.

The term "computer-readable medium" as used herein refers to any media that participates in providing instructions to processor 504 for execution. Such a medium may take many forms, including but not limited to, non-volatile media, volatile media, and transmission media. Non-volatile media includes, for example, optical or magnetic disks, such as storage device 510. Volatile media includes dynamic memory, such as memory 506. Transmission media includes coaxial cables, copper wire, and fiber optics, including the wires that comprise bus 502. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector coupled to bus 502 can receive the data carried in the infra-red signal and place the data on bus 502. Bus 502 carries the data to memory 506, from which processor 504 retrieves and executes the instructions. The instructions received by memory 506 may optionally be stored on storage device 510 either before or after execution by processor 504.

Further, it should be appreciated that a computer 500 may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

In various embodiments, replicate aliquots of a sample can be loaded into a plurality of support regions to determine the melting temperature, $T_m$, of the each well. Ideally, these temperatures should be identical throughout the wells, given that the samples are replicates. In practice, variations in the analysis system, for example, but limited by, non-uniformity of heating elements of the analysis system, create variations in the set of replicates. According to various embodiments of methods for analyzing HRM curve data, such HRM curve data using replicates may be used as a calibration set of data. In various embodiments of step 10 of method 100 of FIG. 1 and step 105 of method 200 of FIG. 2, such a plurality of melting points comprises a plurality or set of calibration melt curve data (CMCD). Similarly, for various embodiments of step 20 of FIG. 1 and step 110 of FIG. 2, unknown samples of interest for analysis may be dispensed into a plurality of support regions of a sample support device to determine the melting temperature of the unknown samples. Such a plurality of melting points comprises a plurality or set of experimental melt curve data (EMCD).

Figure 2:
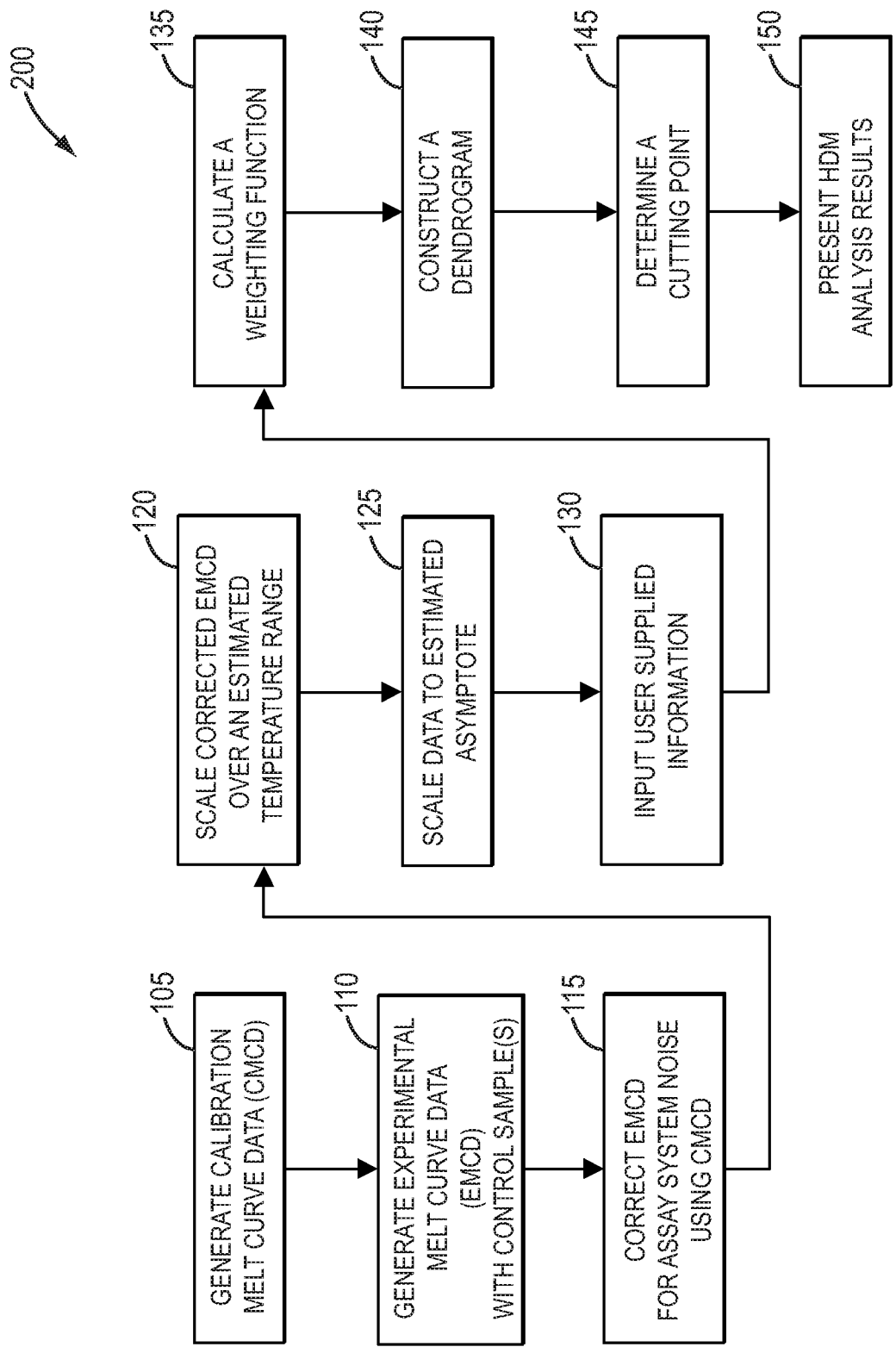
FIG. 2 is a flow chart that depicts various embodiments of methods for the analysis of HRM curve data.

According to various embodiments of methods for analyzing HRM curve data, as depicted in step 30 of method 100 of FIG. 1 and step 115 of method 200 of FIG. 2, signal processing steps may be applied to the raw HRM curve data in advance of subsequent steps, such scaling, curve fitting, and cluster analysis. Such signal processing steps may include the correction of the EMCD with respect to assay system variance or noise. Sources of assay systems noise may include, for example, but not limited by, thermal non-uniformity inherent in thermal cycler system, excitation source non-uniformity, and detection source noise. As depicted in step 30 of FIG. 1 and step 115 of FIG. 2, according to various embodiments, signal processing steps may be applied to the raw HRM curve data in advance of steps, such as steps 40 and 50. In various embodiments, the correction of the EMCD by the CMCD may be performed after steps, such as steps 40 and 50.

As previously stated, as the calibration melt curve data set is generated from replicates of the same sample dispensed in support regions of a sample support device, the variations in the calibration data are due to the inherent assay system noise. Accordingly, the information in the calibration melt curve data can be used to correct the experimental melt curve data for system noise. As one of ordinary skill in the art is apprised, such calibration data may be generated in a variety of ways. For example, but not limited by, an end user may run a calibration set of samples on a separate plate in a separate run from a experimental set of samples in a separate run. Alternatively, an end user may run the run a calibration set of samples on the same plate in the same run as the experimental set of samples. Alternatively, an end user may run the calibration samples and experimental samples as a duplex reaction, where a single well may have a calibration sample and an experimental sample.

According to various embodiments of step 30 of method 100 of FIG. 1 and step 115 of method 200 of FIG. 2 for the correction of EMCD using the CMCD, a reference sample region in the EMCD may be selected. In various embodiments, the frequency plot of the intensities of the sample regions, such as a well, in a sample support device may be determined, and a sample region within two standard deviations of the peak intensity of the EMCD may be selected as a reference sample region. In various embodiments, the reference sample region of the EMCD corresponding to the greatest intensity may be selected, however any sample region within two standard deviations would not be an outlier; i.e. either too dim or to bright, for the purpose of selecting a reference sample region, such as a well. According to various embodiments for correcting system noise as indicated in step 30 of FIG. 1 and step 115 of FIG. 2, the corresponding sample region for the CMCD is then selected as a CMCD reference sample region, such as a well. In various embodiments, a difference from the CMDC reference sample region to any sample region on the sample support may be calculated for any point along the HRM curve data, or any form of the HRM curve data, such as, but not limited by, derivative data. This correction of the variation of the sample support regions over the sample support device due to assay system noise may then be applied to the EMCD. Other types of approaches may be used to determine a correction factor. For example, an average of the intensities of the CMCD may be taken over the entire CMCD sample set. For any specific sample region of the CMCD, a correction may be determined by subtracting the sample region intensity from the average. That correction may then be applied to the corresponding sample region of the EMCD.

According to various embodiments, in step 40 of method 100 of FIG. 1 and step 120 of method 200 of FIG. 2, HRM curve data may be processed to remove information that is not relevant for defining true differences among HRM curves having melting temperatures that are different by only fractions of a degree, by scaling the data over an estimated temperature range. As previously stated, various embodiments, step 40 of FIG. 1 and step 120 of FIG. 2 may be done on the corrected EMCD after step 30 and step 120, while in other embodiments, step 40 may be performed on the CMCD and EMCD before the step of correcting the EMCD for assay system noise.

Figure 5:
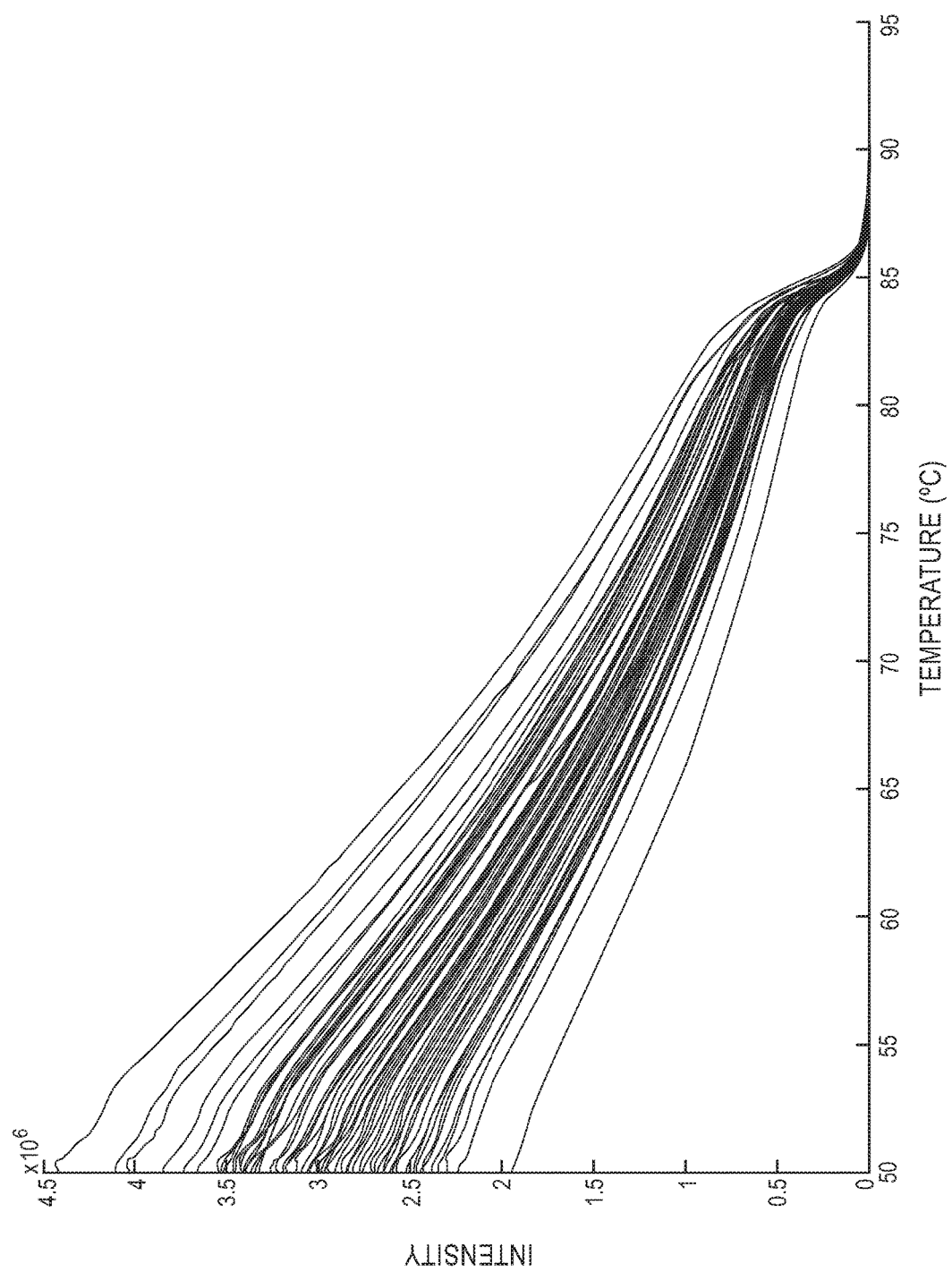
FIG. 5 depicts a series of HRM curves for a set of calibration data.

In FIG. 5, a set of CMCD is used to illustrate various embodiments of step 40 of FIG. 1 and step 120 of FIG. 2. The CMCD shown in FIG. 5 represents raw melt curve data for 96 replicates of a sample, where intensity of the signal is plotted as a function of temperature. Between 50° C. and 55° C., in the low temperature region of the curve, there are deviations from linearity that are artifacts, which are irrelevant to the melt curve data. Further, by inspecting FIG. 5, it is apparent that the melting occurs in a region of between about 70° C. to about 90° C., and that intensity approaches zero at temperatures above the melt. Additionally, the region from about 55° C. to about 80° C. a monotonic decrease in intensity is apparent. This is due to a decrease in the light emitted from the replicates as a result of the temperature dependence of dye emission, which is known to be an inverse relationship (i.e. dye emission decreases as temperature increases).

According to various embodiments methods for analyzing HRM curve data as depicted in step 40 of method 100 of FIG. 1 and step 120 of method 200 of FIG. 2, curve-fitting of the calibration data may be done based on the observations that the region between about 50° C. to about 55° C. contains artifacts, the region between 55° C. to about 80° C. should be linear, the melt occurs between about 70° C. to about 90° C., and the high temperature region above the melt approaches zero. In various embodiments, the curve-fitting of the calibration data may additionally use the information from a reference well in the calibration set. For example, a reference well may be selected as the initially brightest well in a calibration set before the HRM curve analysis is run. A first derivative may be taken on the reference well melt curve data after the analysis is complete. The width of the first derivative peak of a reference well may be used in conjunction with the observation that the melting occurs in a region of between about 70° C. to about 90° C. to define the abscissa. Additionally, given that it is known that the region between 55° C. to about 80° C. should be linear, the ordinate may be scaled using a relative scale, wherein a maximum value of the ordinate scale is set by an intercept of the low temperature end of the melt curve data with the ordinate, and should approach zero at the high temperature range of the melt curve profile.

Figure 6:
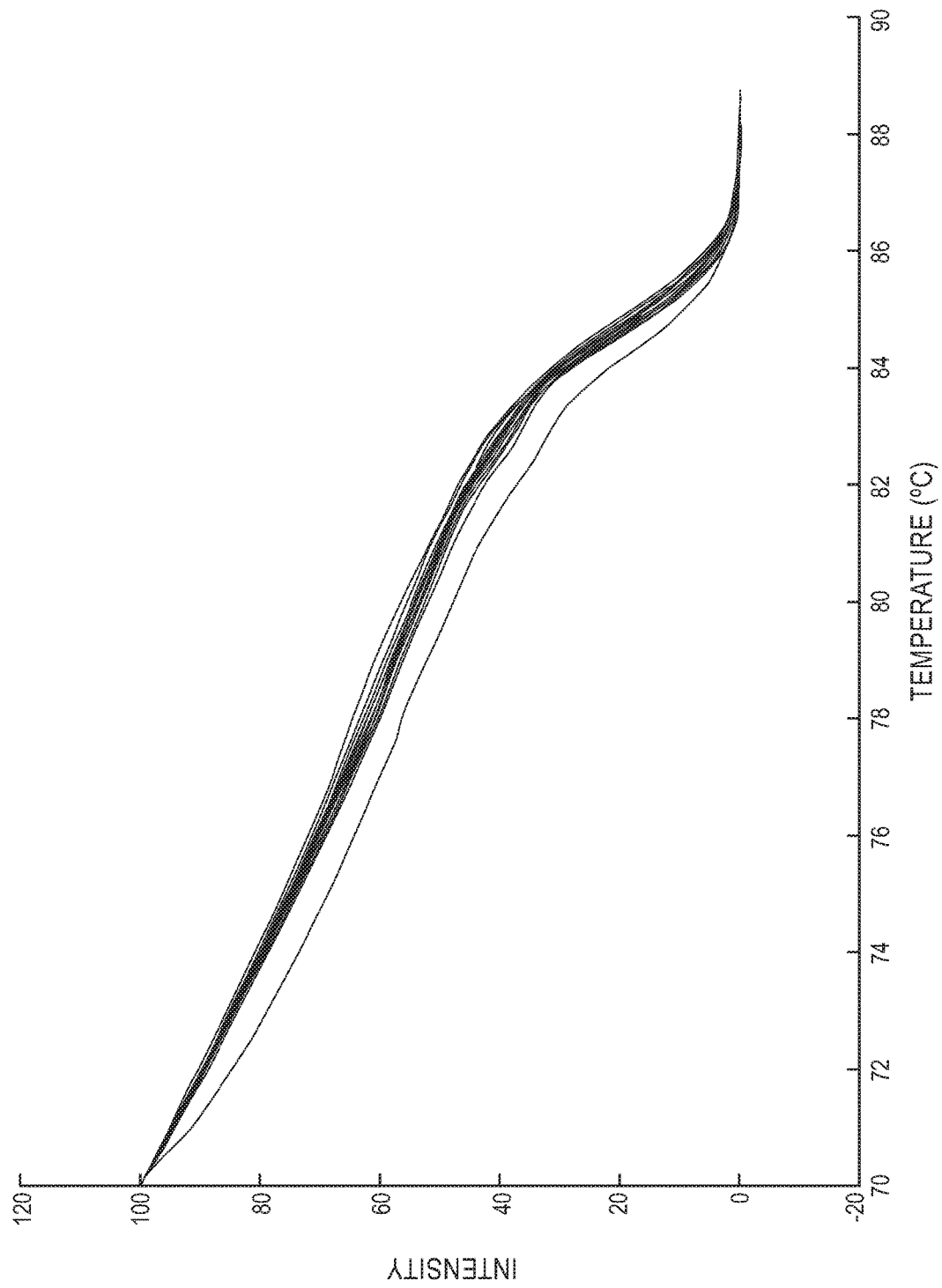
FIG. 6 depicts the series of graphs of FIG. 5 taken over an estimated temperature range according to various embodiments of methods for the analysis of HRM curve data.

According to various embodiments of step 40 of FIG. 1 and step 120 of FIG. 2, for the purpose of illustration, the CMCD of FIG. 5 has been scaled to produce the melt curve data shown in FIG. 6. For FIG. 6, the calibration data of FIG. 5 have been fit to an abscissa scaled to between about 70° C. to about 88° C. Additionally, the linear portion of the low melt end of the CMCD have been fit to 100 at intercept at the low temperature end of the scale, and approach zero at the high temperature range of the melt curve profile.

In various embodiments of methods for analyzing HRM curve data, in addition to the curve-fitting of step 40 of FIG. 1 and step 120 of FIG. 2, additional curve-fitting steps maybe applied to either the CMCD or EMCD. For example, as indicated in step 50 of method 100 of FIG. 1 and step 150 of method 200 of FIG. 2, according to various embodiments, it may be desirable to estimate an asymptote at the low temperature end of the curve for the purpose of detecting differences in data sets of melt curve data that have melting temperatures that vary by only fractions of a degree. Various embodiments for estimating an asymptote for the low temperature end of the melt curve data are depicted in FIGS. 7A and 7B. As previously stated, various embodiments, additional curve-fitting steps such as steps 40 and 50 of method 100 of FIG. 1 and steps 120 and 125 of method 200 of FIG. 2 may be done on the corrected EMCD after step 30 of FIG. 1 and step 115 of method 200 of FIG. 2. According to other embodiments, additional curve-fitting steps such as steps 40 and 50 of FIG. 1 and steps 120 and 125 of FIG. 2 may be performed on the CMCD and EMCD before the step of correcting the EMCD for assay system noise.

In FIG. 7A, for various embodiments of step 50 of FIG. 1 and step 125 of FIG. 2, line B may be extrapolated from a melt curve A by selecting a linear portion over a narrow region of the low temperature melt range. The linear portion may be selected, according to various embodiments, by an interval of a temperature change at a defined temperature point. According to various embodiments, the defined temperature point may be selected using the first derivative data, and defining a transition region, as for example, but not limited by, the full width at half the maximum of the first derivative peak. As one of ordinary skill in the art is apprised, such a transition region corresponds to an interval of two standard deviations about the midpoint of the first derivative curve. As such, other intervals about the curve may also be selected. In various embodiments, a temperature point may be selected at the low temperature end of the defined transition region, as the low temperature region is known to be linear. According to various embodiments of step 50 of FIG. 1 and step 125 of FIG. 2, after a temperature point is selected, an interval from the point containing enough data points to extrapolate a line is selected. In that regard, the interval would correspond to at least two data points. According to various embodiments, the interval may be at least about 0.1° C. In various embodiments of step 50 of FIG. 1 and step 125 of FIG. 2, the interval may be at least about 0.5° C. In still other embodiments of step 50 of FIG. 1 and step 125 of FIG. 2, the interval may be at least about 1° C.

Figure 8:
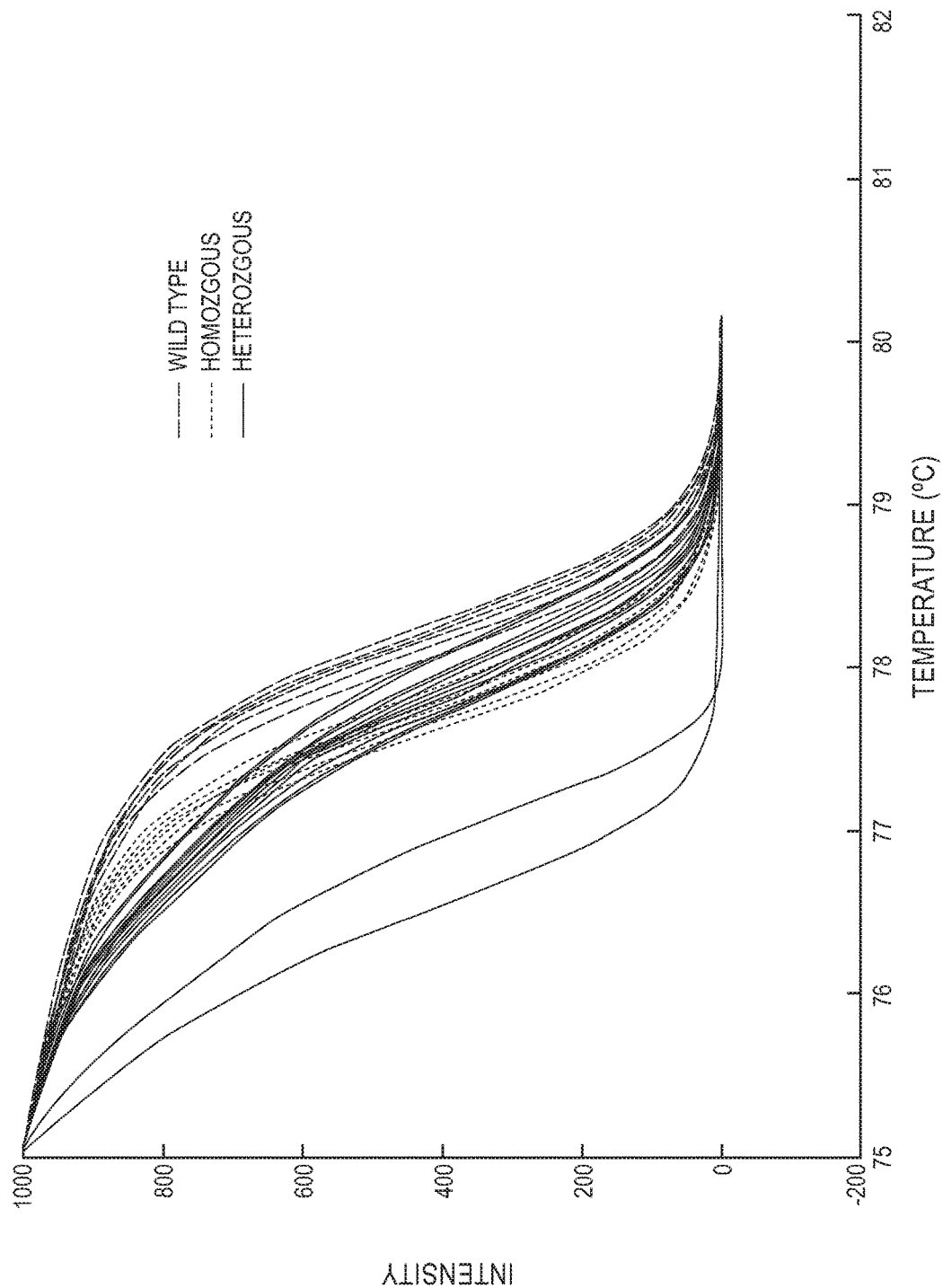
FIG. 8 depicts a set of data that has been corrected for assay system variance or noise according to various embodiments of methods for the analysis of HRM curve data.

For example a temperature point of about 70.0° C. may be selected, with an interval of plus or minus 0.5° C. around the temperature point. From this narrow linear region, a line, such as line B in FIG. 7A can be extrapolated. An algorithm, such as the subtraction of melt curve A and line B, can be used to evaluate a point where the two functions deviate by preset limit. For example, but not limited by, when the difference between the two curves is at least as great as, for example, twice the assay noise, then the calculated difference may indicate a significant difference. Alternatively, in various embodiments of step 50 of FIG. 1 and step 125 of FIG. 2, other methods for determining a point where the two functions deviate by preset limit, such as the method for detecting nonlinearity in analog circuit analysis, may be used. Such a preset limit is designated as point C in FIG. 7A. Point C defines a point through which line D is drawn horizontally through the ordinate, thereby defining an estimated asymptote for the low temperature region, according to various embodiments of step 50 of FIG. 1 and step 125 of FIG. 2. The calibration melt curve A is then fit accordingly to this asymptote, line D, as shown in FIG. 7B. A set of EMCD, processed according to various embodiments of steps 10-50 of method 100 of FIG. 1 and method steps 105-125 of 200 of FIG. 2 is shown in FIG. 8. The correction of the EMCS in this example using a set of CMCD results in the ready clustering of genotypes, for the example, is shown in FIG. 8.

Various embodiments of cluster analysis algorithms may be utilized in various methods for the analysis of HRM curve data. As indicated in steps 60-80 of method 100 of FIGS. 1 and 135-145 of method 200 of FIG. 2, various embodiments of cluster analysis methods may utilize an unsupervised learning algorithm, which separates HRM curves into different clusters based on intrinsic properties of HRM curves. Accordingly, various embodiments of method 100 of FIG. 1 and method 200 of FIG. 2 may automatically separate a set of input HRM curves into different groups or clusters without the use of a control sample.

More specifically, various embodiments of method 100 of FIG. 1 utilize unsupervised learning algorithms, which do not require any user input. However, as will be discussed more subsequently, for various embodiments of method 200 of FIG. 2, the user may specify a sample or samples as a control. For example, for genotyping analyses, a user may specify a sample as having a genotype such as "wild type", "homozygote", and "heterozygote", or other labels identifying a genotype. According to various embodiments; once a user has input such information, they may also select or associate additional HRM curves with the user specified control or controls. Accordingly, various embodiments of method 200 will assign high resolution melts curves not associated with a control or controls into other variant groups according to clustering results. For various embodiments of method 200, a control may be a sample or samples for which the user has specific information, such as known genotype, SNP, and the like. For various embodiments of method 200, a control or may be a label rather than a prototype of a particular group of HRM curves. For example, according to various embodiments of method 200, the user can specify two HRM curves to be "wild type" even though the two high resolution melt curves appear to have very different shapes based on human observation. Then according to various embodiments of method 200, the analysis will stop the clustering process when further iteration will produce results that are contradictory to the user specified classification.

Figure 9:
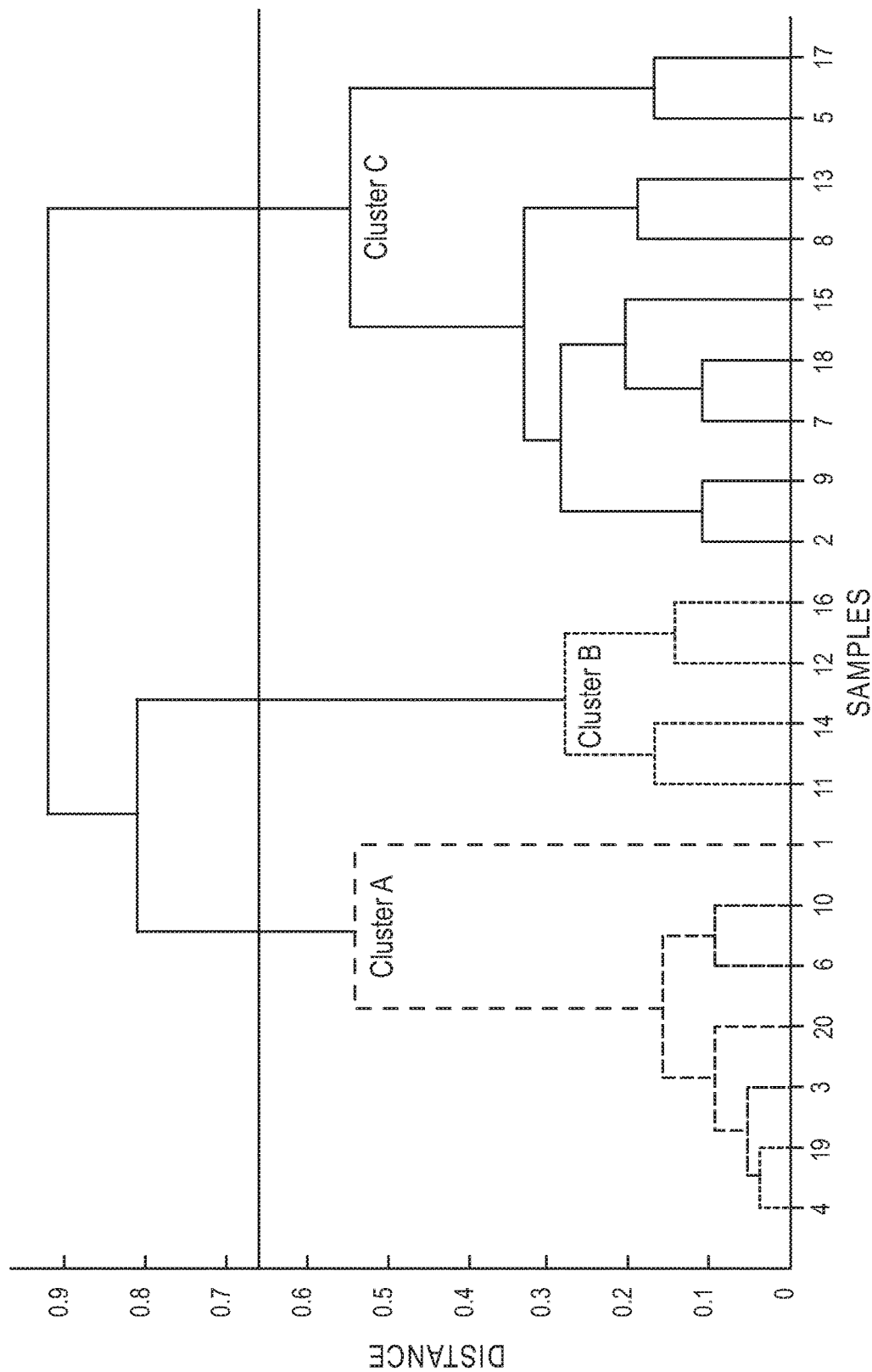
FIG. 9 depicts a conceptual rendering of a dendrogram useful for various embodiments of cluster analysis for HRM curve data.

Various embodiments of step 70 of method 100 of FIG. 1 and step 140 of method 200 of FIG. 2, may utilize cluster analysis methods as depicted in FIG. 9, which is a conceptual rendering of hierarchical clustering analysis that can be represented using a dendrogram. In FIG. 9, a dendrogram constructed using 20 samples is shown. A dendrogram is a tree-like plot where each clustering step is represented as a fusion of two tree nodes into a single one at each step. The nodes represent clusters obtained at each step of hierarchical clustering. Nodes may be described as leaf nodes or interior nodes, which are clusters. For example, in FIG. 9, the node at level 1, in which sample 4 and sample 19 are merged into a cluster is a leaf node, while the node at level 18 is an interior node merging cluster A and cluster B. In various embodiments, at each step two clusters may be grouped based on a calculated distance, and then grouping two clusters based on a minimum distance. As will be discussed in more detail subsequently, a distance can calculated between HRM curves and between clusters. Examples of functions for calculating distance for HRM curves include, but are not limited by the weighted distance, Minkowski distance, Pearson correlation distance, cosmic angle distance, and square distance functions. Examples of methods for calculating the distance between clusters includes, but is not limited by a centroid-based, minimum-based, and average-based method. According to various embodiments of step 70 method 100 of FIG. 1 and step 140 of method 200 of FIG. 2, the hierarchical clustering algorithm proceeds until there is only one cluster. The number of levels in a dendrogram is one less than the number of samples. For example, in FIG. 9, there are 20 samples and 19 levels.

According to various embodiments of step 70 of method 100 of FIG. 1 and step 140 of method 200 of FIG. 2, all of the information in the corrected and rescaled HRM curves may be used to create a dendrogram for the purpose of creating clusters using embodiments of a hierarchical clustering algorithm. According to various embodiments, two clusters $C_i^l$ and $C_j^l$ may be merged if the distance, $d_{i,j}^l$, between $C_i^l$ and $C_j^l$ is the smallest among all pairs of nodes on the same level l. In various embodiments, a distance between leaf nodes may be calculated using, for example, but not limited by, the following equation:

$$d_{i,j}^l = \sum_{\alpha=1}^{M} w_\alpha \times (m_\alpha^i - m_\alpha^j)^2 \qquad \text{Eq. 1}$$

Where: $d_{i,j}^l$=the distance between two clusters, $C_i^l$ and $C_j^l$.
M=the number of data points in a HRM curve
$m_\alpha^i$=the $\alpha^{th}$ data point of HRM curve i
$m_\alpha^j$=the $\alpha^{th}$ data point of HRM curve j; and
$w_\alpha$=the $\alpha^{th}$ data point of a weighting vector For interior nodes, or clusters, the distance between clusters may be determined by, for example, a centroid-based, minimum-based, and average-based method, as previously mentioned. According to various embodiments utilizing a centroid-based method, the location of the centroid is determined for all sets of clusters at the same level, and the distance between the centroids is determined. In various embodiments utilizing a minimum-based method for grouping clusters, an iterative method calculating the distance between every pair of discrete members of two clusters is done, and the minimum distance calculated is selected as the distance between the two clusters. The average-based method is similar to the minimum-based method, except the average distance between each member in a pair of clusters is calculated to determine the distance between two clusters. For each case, a distance is determined for every pair of clusters at the same level, and two clusters are grouped based on the minimum distance calculated.

In summary, according to various embodiments of method 100 of FIG. 1 and of method 200 of FIG. 2, in order to construct a dendrogram, the determination of distances between leaf nodes and interior nodes, or clusters, may be calculated as previously described. However, according to various embodiments of method 100 of FIG. 1 and of method 200 of FIG. 2, and as shown in Eq. 1, a determination of a distance between two leaf nodes utilizes a weighting function. Therefore, according to various embodiments of step 60 of method 100 of FIG. 1 and step 135 of method 200 of FIG. 2, a calculation of a weighting function is done in order that the calculation of distances between members of a leaf node may be done. For example, but not limited by, according to various embodiments of step 60 of method 100 of FIG. 1 and step 135 of method 200 of FIG. 2, the calculation of a weighting function may be given by:

$$w_\alpha = \frac{\sum_{k=1}^{N} m_\alpha^k}{N} \qquad \text{Eq. 2}$$

Where: $w_\alpha$=the $\alpha^{th}$ data point of a weighting vector
N=the number of HRM curves; and $$\sum_{k=1}^{N} m_\alpha^k =$$

the sum over the $\alpha^{th}$ data points for $N$ $HRM$ melt curves in a data set Additionally, as the weighting function is subject to the normalization condition:

$$\sum_{\alpha=1}^{M} w_\alpha = 1 \qquad \text{Eq. 3}$$

Then, first a sum over all $\alpha^{th}$ data points of a weighting vector for all data points is calculated:

$$W = \sum_{\alpha=1}^{M} w_\alpha \qquad \text{Eq. 4}$$

So that $w_\alpha$, the $\alpha^{th}$ data point of a weighting vector is given by:

$$w_\alpha = \frac{w_\alpha}{W} \qquad \text{Eq. 5}$$

Figure 10A:
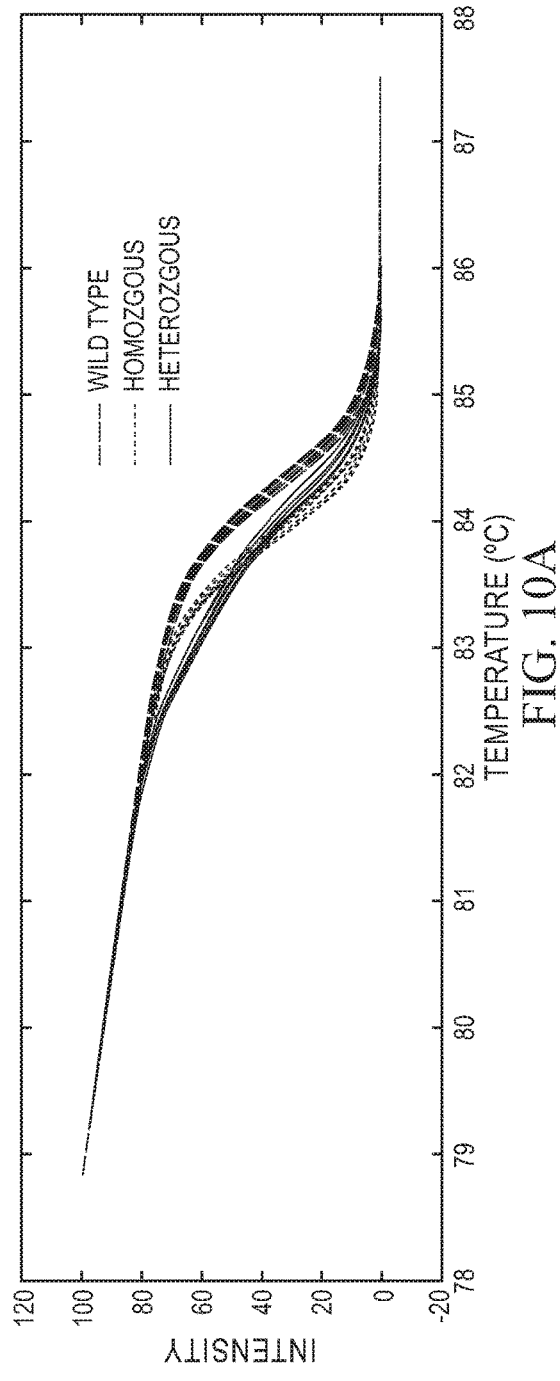
FIGS. 10A and 10B depict an exemplary set of EMCD for genotyping analysis on which various embodiments of a method for the analysis of HRM curve data may be performed
Figure 10B:
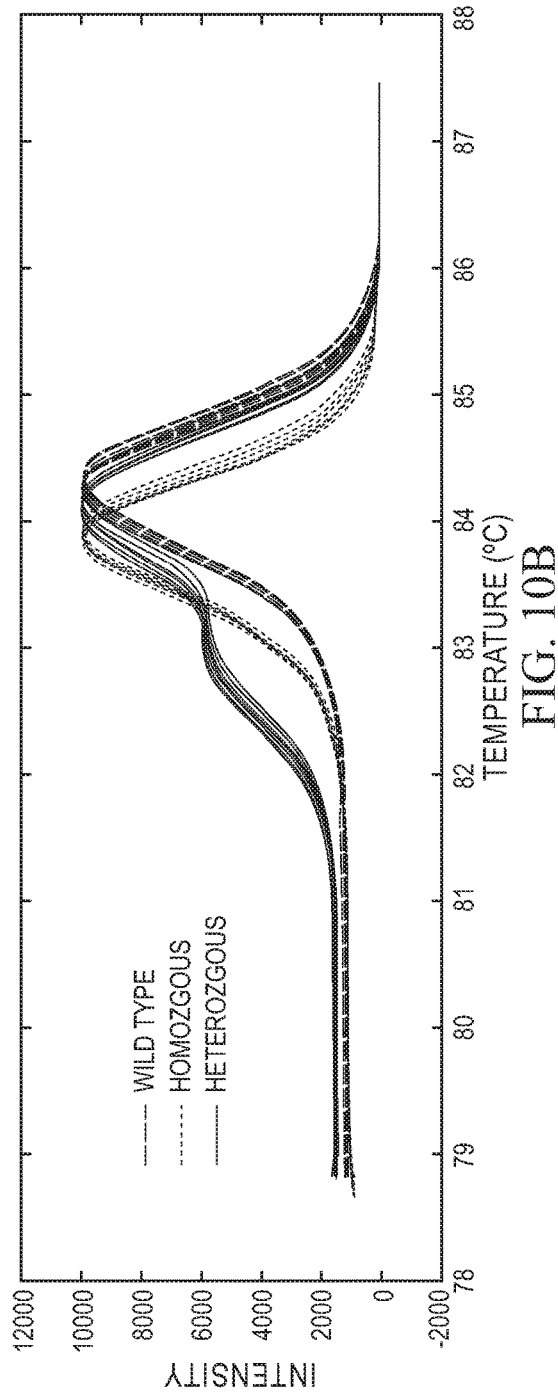

For the purpose of illustration of various embodiments of methods for the analysis of HRM curve data, in FIG. 10A and FIG. 10B, an exemplary set of EMCD for 27 samples is shown. For this exemplary set of EMCD, the analysis was for genotyping, though one of ordinary skill in the art would recognize that various embodiments of methods of the analysis of HRM curve data are widely applicable to a numerous assays, as previously discussed. In FIG. 10A, the corrected and rescaled sample EMCD are presented, while in FIG. 10B, the second derivative of the EMCD shown in FIG. 10A is presented. For various embodiments of methods for analyzing HRM curve data, either corrected and rescaled EMCD, such as those shown in FIG. 10A, or second derivative EMCD, such as those shown in FIG. 10B, may be used.

Figure 11:
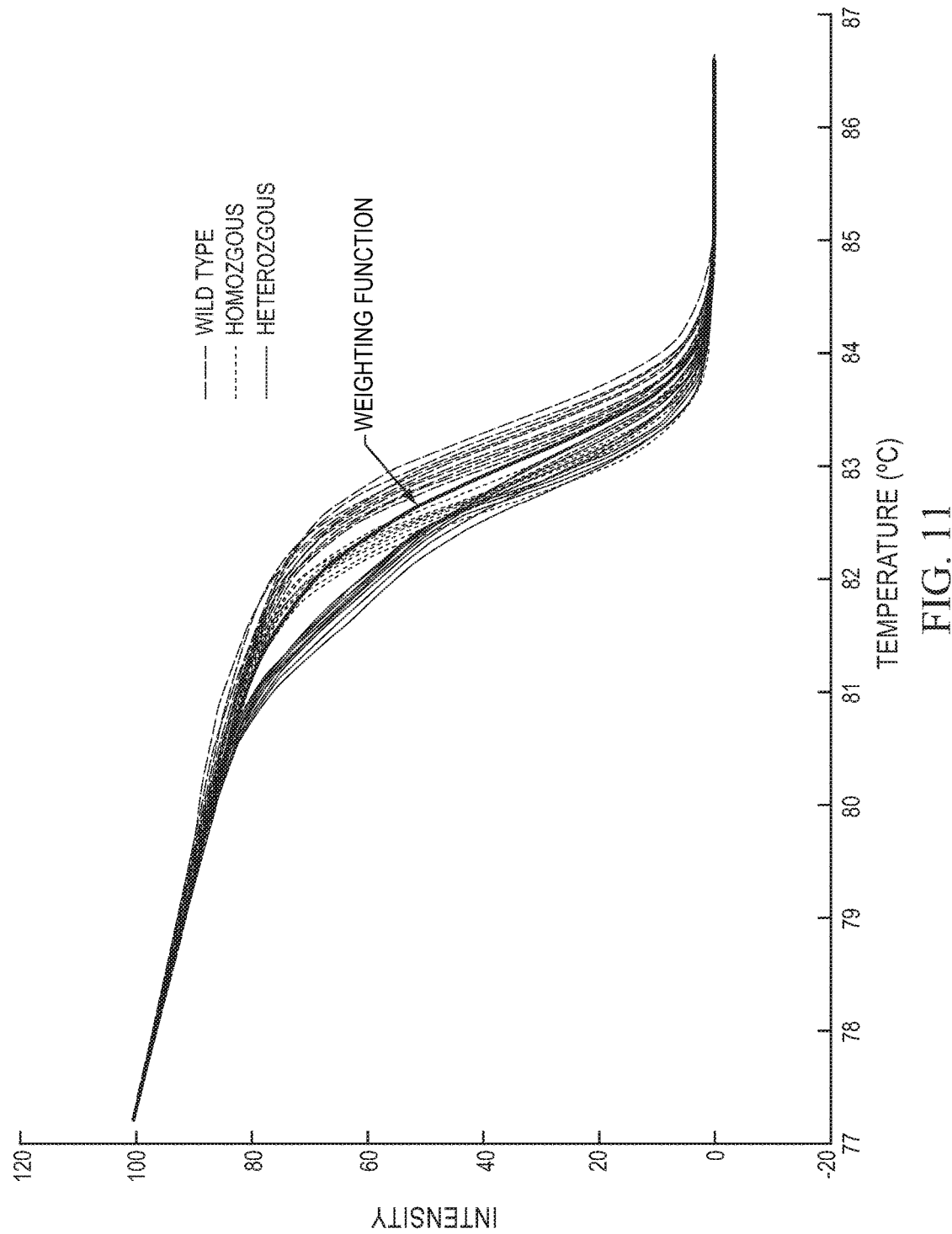
FIG. 11 depicts a weighting point curve constructed from the point-by-point calculation of a weighting function according to various embodiments of a method for the analysis of HRM curve data.

As given in Eq. 1-Eq. 5, all the information, or data points, generated for the HRM curves may be used not only in a calculation of distance between two leaf nodes, but also for the calculation of a weighting function. According to various embodiments of step 60 of method 100 of FIG. 1 and step 135 of method 200 of FIG. 2, such a weighting function may be graphically demonstrated for the exemplary analysis of 27 genotyping sample HRM curves, as displayed in FIG. 11. As one of ordinary skill in the art is apprized, there may be a variety of ways to approach creating a weighting function for clustering algorithms. For example, for HRM curve data, the transition region is an information rich region including the melting temperature. Arguably, it would be logical to give the data points in such an information rich region more weight. As such, a weighting function could be so constructed.

Surprisingly, the weighting function given by Eq. 2 resulted in enhancing the calculation of the distances between HRM curves for various embodiments of method 100 of FIG. 1 and of method 200 of FIG. 2. For example, in FIG. 11, and in reference to Eq. 1 and Eq. 2, it can be seen that for in the region between about 80° C. to about 81.5° C., the differences between data points in the sets of HRM curves tend to be small. However, the weighing factor tends towards a maximum in those that region. The net result is that differences in the curve in that region are amplified. Additionally, in the region between about 83° C. to about 84.5° C., the quality of the data is poorer, due to increasing noise with decreasing signal. However, the weighting factor tends towards a minimum in that region. The net result is that data points in that region have less impact on the determination of distance between two HRM curves. In that regard, various embodiments of a weighting function utilizing all the information in all data points in a set of HRM curves produced results that were counter-intuitive to that expected in comparison to other possible embodiments, such, but not limited by, weighting the data points in the information rich transition region.

According to various embodiments of step 80 of method 100 of FIG. 1 and of step 145 of method 200 of FIG. 2, after a dendrogram has been constructed, then a cut level may be determined. As will be discussed in more detail subsequently, various embodiments of method 100 may determine the cut level without the need for user inputted information, as shown in step 130 of method 200.

Figure 12:
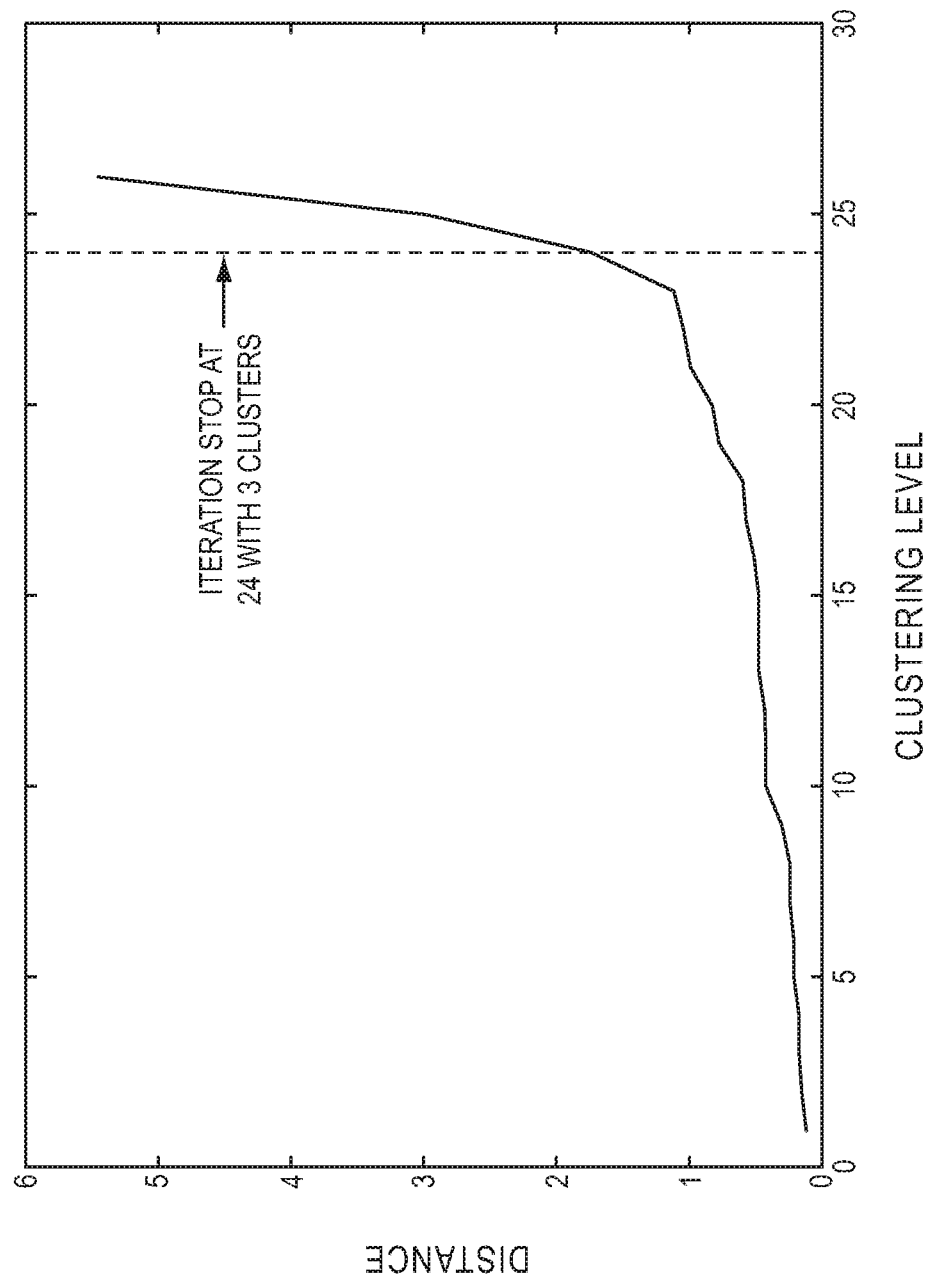
FIG. 12 is a graph depicting an embodiment for the determination of a cut level on an exemplary set of EMCD for genotyping analysis.

For various embodiments of step 80 of method 100, a cut level may be determined as graphically depicted in FIG. 12. The relationship between the distance calculated at every step of constructing a dendrogram as a function of the level may be determined. This is as shown in FIG. 12 for the exemplary set of 27 genotyping HRM curves, which were presented in FIG. 10A and FIG. 10B. As the leaf nodes are merged into clusters with interior nodes, the minimum distance for merging increases at every level. As the samples are merged into a single cluster, this fairly linear relationship has a significant change in slope, as can be seen by inspecting FIG. 12. The root-mean-square (RMS) error for every level may be calculated as:

$$e^\alpha = \sum_{l=1}^{N-1} \left( \overline{d}^l - d^l \right)^2 \qquad \text{Eq. 6}$$

The cut level is determined when the RMS error is a minimum. For the exemplary set of 27 genotyping HRM curves, as shown in FIG. 12, this occurs at level 24, producing 3 clusters.

Additional approaches for the determination of cut level are possible. For example, according to various embodiments, a maximum allowable merge distance (MAMD) can be computed from control samples. In various embodiments, the MAMD is the maximum distance between all possible pairs of distinct control samples, and the cutting level is the maximum level in which merge distance between clusters is less than MAMD. In various embodiments, one approach is to find maximum cutting level in which user specified control samples belong to different clusters. According to various embodiments of methods using a cut level with specified control samples, such various algorithms may stop merging when further merging will violate user control inputs.

Figure 13:
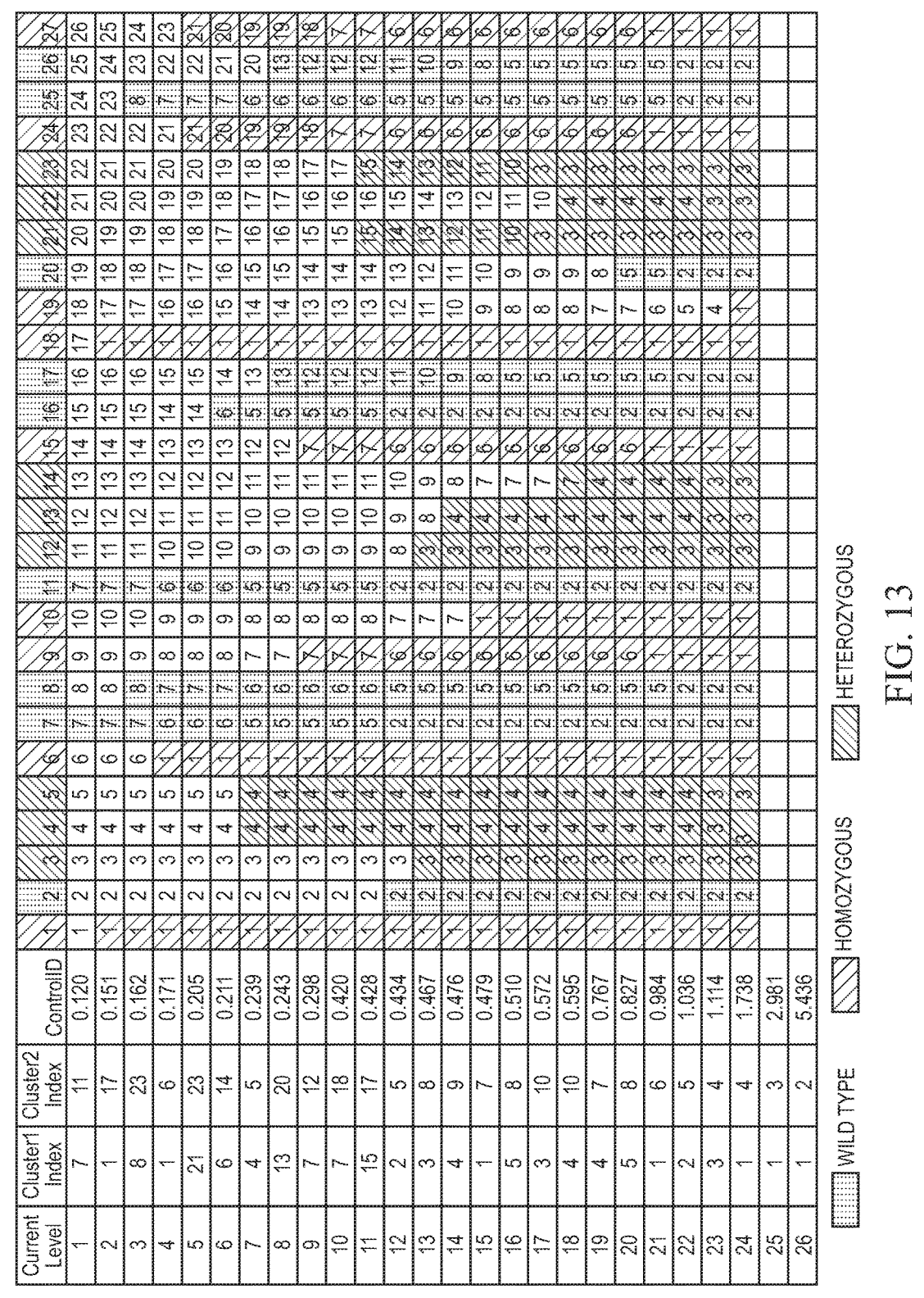

In FIG. 13, the results are shown for the exemplary set of 27 genotyping HRM curves produced with an embodiment of method 100 of FIG. 1, utilizing an unsupervised hierarchical clustering algorithm. In FIG. 13, starting from the left hand side, the first column is the iteration step. The second and the third columns show the two clusters having the minimum distance as displayed in column 4. Starting at the first iteration step, two leaf node clusters, representing sample 1 and sample 7 are merged, as it is clear from inspection of column 4 that they represent a minimum distance in the set of distances calculated for the 27 samples. Since cluster 7 and 11 has the minimum distance of 0.120, they are merged, i.e. cluster 11 is relabeled as cluster 7, and the new clusters are renumbered, so that we now only have 26=27−1 clusters, as shown in the last sample column at the first iteration step, or level 1 of the dendrogram formed for the set of 27 samples. At level 24, in reviewing the results across the row, it is apparent that the samples have been merged into 3 clusters. This is also visually reinforced by inspecting the graphical representation of the 27 samples in FIG. 10A and FIG. 10B, which for this exemplary set of HRM curves, is comparable to the results generated using an embodiment of method 100 of FIG. 1.

In comparing method 100 of FIG. 1 and of method 200 of FIG. 2, method 200 of FIG. 2 has an additional step, shown at step 130. According to various embodiments of method 200 of FIG. 2, a user can input information into the HRM curve data analysis method before a hierarchical clustering algorithm is run in steps 135-150 of method 200. In that regard, various embodiments of method 200 may allow for a supervised cluster analysis, in contrast to the unsupervised clustering analysis provided by various embodiments of method 100.

For the purpose of illustration of various embodiments of method 200 of FIG. 2, an exemplary set of HRM curves for 92 samples is shown in FIG. 14A and FIG. 14B. Similar to representation of the 27 samples shown in FIG. 10A and FIG. 10B, in FIG. 14A, the corrected and rescaled sample HRM curves are presented, while in FIG. 14B, the second derivative of the HRM curves shown in FIG. 14A is presented. What is displayed in both figure set is the output of the clustering algorithm which is solely based on the intrinsic characteristics of the melt curves, using an embodiment of utilizing an unsupervised hierarchical clustering algorithm. It is clear by inspecting FIG. 14A and FIG. 14B that 5 clusters have been identified. The cluster labeled "variant 4" includes curve 40, representing a sample positioned in well D8 of a microtiter plate, and is positioned as the upper most curve in FIG. 14A, or the outer most curve in FIG. 14B. The other member in the cluster designated "variant 4" corresponds to curve 76, representing a sample that was positioned in well G8 of a microtiter plate.

Figure 15A:
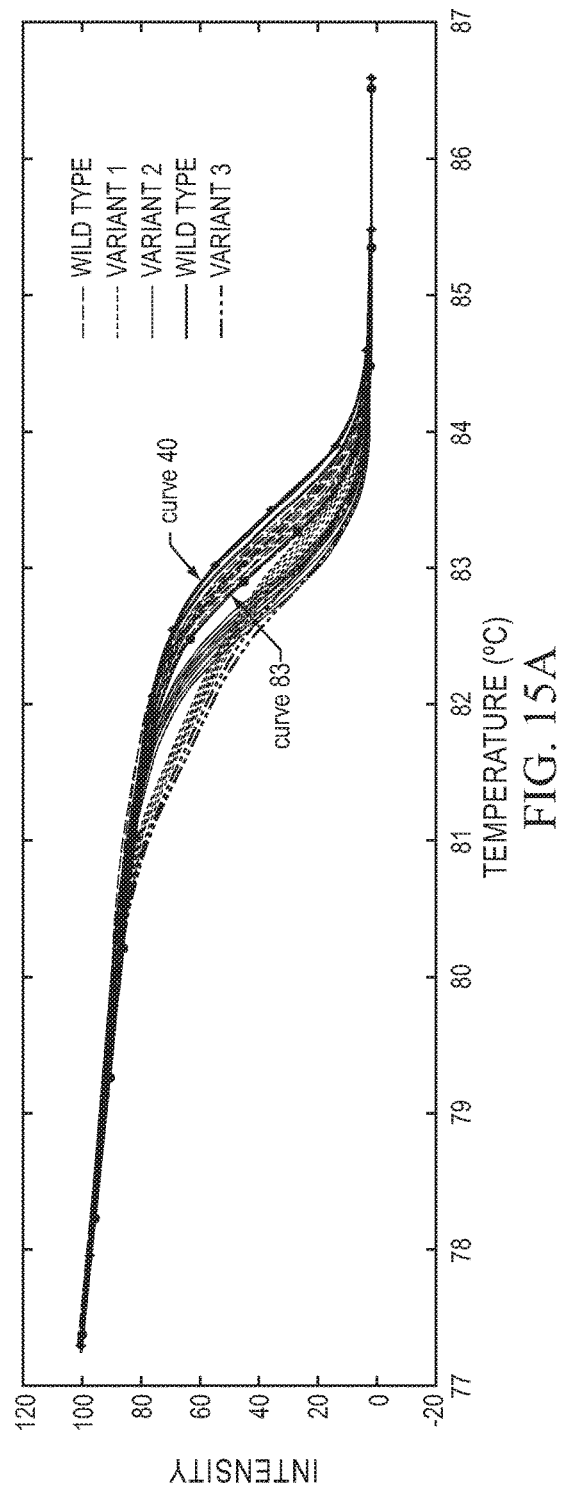
FIGS. 15A and 15B depict an association of an HRM curve genotyping control with selected samples according to various embodiments of a method for the analysis of HRM curve data.
Figure 15B:
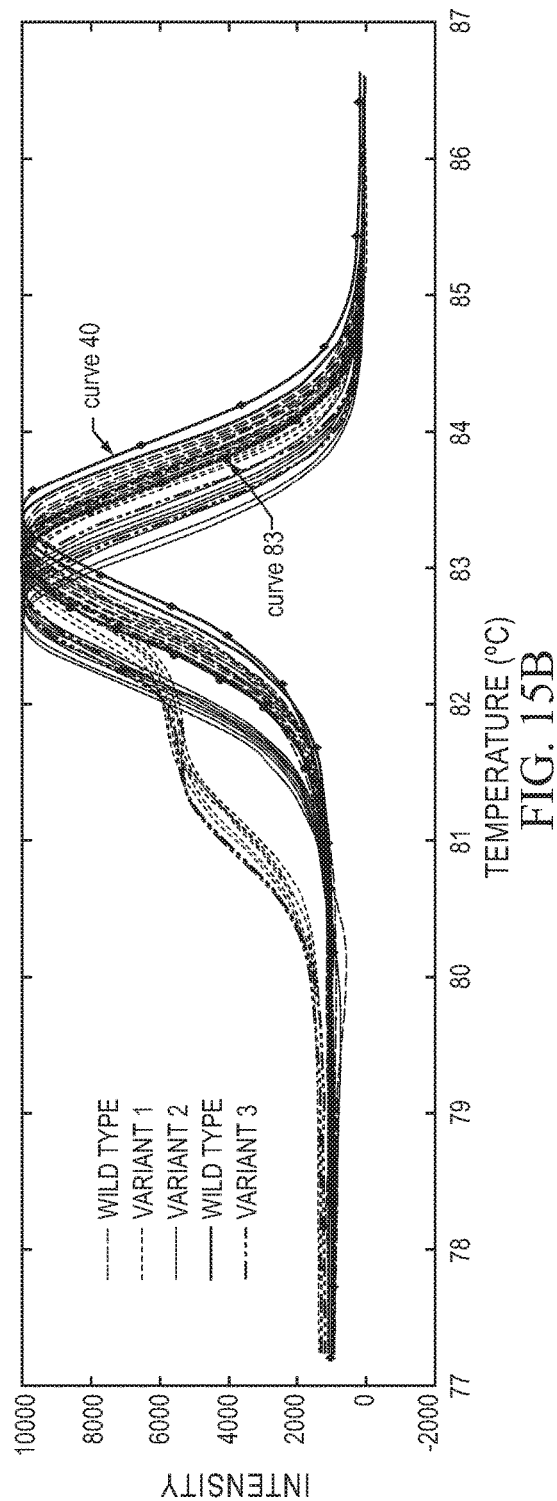

In FIG. 15A and FIG. 15B, the designation of sample identification for association with a set of samples may be provided by a user, according to various embodiments of step 130 of method 200 of FIG. 2. For this example, curve 40, for sample D8 was identified by a user as wild type (WT), and the entire set of variant 2 and variant 4 samples have been associated with this identification, as indicated in the legend for FIG. 15A and FIG. 15B. According to various embodiments of method 200, after user information is inputted regarding the designation of sample identification of at step 130 of method 200, the clustering algorithm may cluster the melt curves based on the intrinsic characteristics of the data, and may identify samples in a set of based on user provided information. An example of a clustering output is shown in FIG. 16. In the table shown in FIG. 16, a partial output is shown for the set of samples 39-76 of 92 samples run, which includes curve 40, designated as the sample identified as wild type, and curve 76, which were grouped by the unsupervised embodiment of a clustering algorithm with curve 40 as variant 4. It is clear by inspection of the table that all members that may be grouped by an unsupervised hierarchical algorithm, such as an embodiment of method 100 of FIG. 1, as variant 2 and variant 4 have been clustered together using an embodiment of method 200 of FIG. 2 as wild type (WT) by utilizing information provided by a user. Such sample identification may be provided by a user having knowledge that a specific sample is a control sample, or a that a sample has a verified identity, etc In addition to information, such as the designation of sample identification for association with each member in a set of clustered samples, a user may input other information that may assist in the evaluation of the samples run using HRM analysis. For example, according to various embodiments, the user may additionally identify the limit for the number of clusters that be found in a set of samples. In that regard, when using HRM for genotyping, the user may have a priori knowledge to specify that a limit of, for example, three clusters should be found. Similarly, for mutation detection, a user may have a priori information about the number of clusters that will occur in set of samples. In either of these non-limiting examples, such a priori information may be used for any particular type of analysis done using HRM as additional information useful in the process of determining the number of clusters present in an experimental set of melt curve data. In various embodiments, a user may provide information regarding the identification of an outlier in a set of data. As one of ordinary skill in the art may readily understand, various types of user input may be utilized in various embodiments of a supervised clustering method 200.

According to various embodiments of method 100 of FIG. 1 and method 200 of FIG. 2, a confidence level may be calculated for each discrete HRM determination. For example, but not limited by, a confidence level of the assignment of a sample to a cluster may be calculated as follows: Let $\alpha$ be the average distance of the sample to all other samples within the assigned cluster, and let $\beta$ be the average distance of the sample to all samples within the nearest cluster, then the confidence level is given by:

$$ConfidenceLevel = \left(1 + \frac{\beta - \alpha}{\max(\alpha, \beta)}\right) \times 50 \qquad \text{Eq. 7}$$

For various embodiments of Eq. 7, the confidence level can vary between 0 and 100. A smaller value is undesirable because this corresponds to a case in which the average distance to samples in the cluster is greater than the minimum distance to samples in another cluster.

Finally, for various embodiments of methods for the analysis of HRM curve data, as shown in step 90 of method 100 of FIG. 1 and step 150 of method 200 of FIG. 2, the HRM curve data may be outputted to an user for making determinations of samples analyzed for, for example, but not limited by, genotyping, mutation screening, methylation analysis and single nucleotide polymorphisms (SNPs). Various analyses may, for example, facilitate the identification of mutations associated with specific diseases and conditions, for example, but not limited by, various cancers, thalassemia, neonatal diabetes, and rheumatoid arthritis. Additionally, high resolution melt curve analysis can indicate if multiple products are amplified, non-specific amplification has occurred or if there were assay amplification issues such as the primer-diamer formation. High resolution melt curve analysis can also be used for other biological samples including but not limited by proteins to analyze the signal changes within a sample, or between samples with changing temperature.

As previously mentioned in the discussion of FIG. 3 and FIG. 4, various embodiments of a computer system may be utilized to implement various embodiments of step 90 of method 100 of FIG. 1 and step 150 of method 200 of FIG. 2 for the presentation of data outputted to an user for making determinations of samples using HRM curve data. Such embodiments of a computer system, as mentioned in the discussion of FIG. 3 and FIG. 4, may be utilized in the implementation of displaying, printing and otherwise conveying the presentation of HRM curve data to an end user.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed:

1. A method for analyzing melt curve data, the method comprising:
    providing melt curve data for at least one test sample deposited in a plurality of support regions of a sample support device in thermal cycler system, wherein the melt curve data is an experimental set of melt curve data; and
    providing an interface configured for selecting a weighting function, wherein the weighing function selected is used for giving more weight to datapoints in a transition region including a melting temperature and for the construction of a dendrogram of the corrected experimental set of melt curve data and the interface is further configured for labeling a particular melt curve with a genotype corresponding to a control sample or a verified genotype identity;
    constructing a dendrogram of the corrected experimental set of melt curve data, wherein the dendrogram creates a set of at least one cluster from the corrected experimental set of melt curve data and utilizes the labeled melt curve; and
    determining a cut level of the dendrogram, wherein the cut level determines a final number of clusters from the set of at least one cluster, wherein the cut level stops merging when further merging would result in the labeled particular melt curve belonging to a same cluster as a melt curve labeled with a different genotype.

2. The method of claim 1, wherein the at least one test sample is a plurality of test samples.

3. The method of claim 2, wherein the weighting function utilizes all data points in each of a corrected experimental set of melt curve data for each test sample.

4. The method of claim 2, further comprising:
    providing melt curve data for a calibration sample deposited in a plurality of support regions of a sample support device in a thermal cycler system, wherein the melt curve data is a calibration set of melt curve data; and
    correcting the experimental set of melt curve data using the calibration set of melt curve data.

5. The method of claim 4, wherein the correction is done on a derivative form of the melt curve data.

6. The method of claim 4, wherein the correction of the experimental set of melt curve data using the calibration set of melt curve data is a correction for assay system noise.

7. The method of claim 6, wherein the source of assay system noise is thermal non-uniformity.

8. The method of claim 6, wherein the source of assay system noise is excitation source non-uniformity.

9. The method of claim 6, wherein the source of assay system noise is detection noise.

10. The method of claim 2, further comprising the step of scaling the corrected experimental set of melt curve data over an estimated temperature range.

11. The method of claim 10, further comprising the step of fitting the scaled corrected experimental set of melt curve data to an estimated asymptote for a low temperature region of a melting region of the melt curve data.

12. A system for analyzing melt curve data, the system comprising:
    a computer system in communication with a thermocycling instrument comprising:
        at least one processor; and
        at least one computer-readable medium comprising instructions for pure dye normalization, the instructions being executable by the processor to carry out processing comprising:
        providing melt curve data for at least one test sample deposited in a plurality of support regions of a sample support device in thermal cycler system, wherein the melt curve data is an experimental set of melt curve data; and
        providing an interface configured for selecting a weighting function, wherein the weighing function selected is used for giving more weight to datapoints in a transition region including a melting temperature and for the construction of a dendrogram of the corrected experimental set of melt curve data and the interface is further configured for labeling a particular melt curve with a genotype corresponding to a control sample or a verified genotype identity;

constructing a dendrogram of the corrected experimental set of melt curve data, wherein the dendrogram creates a set of at least one cluster from the corrected experimental set of melt curve data and utilizes the labeled melt curve; and determining a cut level of the dendrogram, wherein the cut level determines a final number of clusters from the set of at least one cluster, wherein the cut level stops merging when further merging would result in the labeled particular melt curve belonging to a same cluster as a melt curve labeled with a different genotype.

13. The system of claim 12, wherein the at least one test sample is a plurality of test samples.

14. The system of claim 13, wherein the weighting function utilizes all data points in each of a corrected experimental set of melt curve data for each test sample.

15. The system of claim 13, further comprising:

providing melt curve data for a calibration sample deposited in a plurality of support regions of a sample support device in a thermal cycler system, wherein the melt curve data is a calibration set of melt curve data; and correcting the experimental set of melt curve data using the calibration set of melt curve data.

16. The system of claim 15, wherein the correction is done on a derivative form of the melt curve data.

17. The system of claim 15, wherein the correction of the experimental set of melt curve data using the calibration set of melt curve data is a correction for assay system noise.

18. The system of claim 13, further comprising the step of scaling the corrected experimental set of melt curve data over an estimated temperature range.

19. The system of claim 18, further comprising the step of fitting the scaled corrected experimental set of melt curve data to an estimated asymptote for a low temperature region of a melting region of the melt curve data.

20. A non-transitory computer-readable storage medium encoded with instructions, executable by a processor, for analyzing melt curve data, the instructions being executable by the processor to carry out processing comprising:

providing melt curve data for at least one test sample deposited in a plurality of support regions of a sample support device in thermal cycler system, wherein the melt curve data is an experimental set of melt curve data; and providing an interface configured for selecting a weighting function, wherein the weighing function selected is used for giving more weight to datapoints in a transition region including a melting temperature and for the construction of a dendrogram of the corrected experimental set of melt curve data and the interface is further configured for labeling a particular melt curve with a genotype corresponding to a control sample or a verified genotype identity;

constructing a dendrogram of the corrected experimental set of melt curve data, wherein the dendrogram creates a set of at least one cluster from the corrected experimental set of melt curve data and utilizes the labeled melt curve; and determining a cut level of the dendrogram, wherein the cut level determines a final number of clusters from the set of at least one cluster, wherein the cut level stops merging when further merging would result in the labeled particular melt curve belonging to a same cluster as a melt curve labeled with a different genotype.

* * * * *